Figure 1:
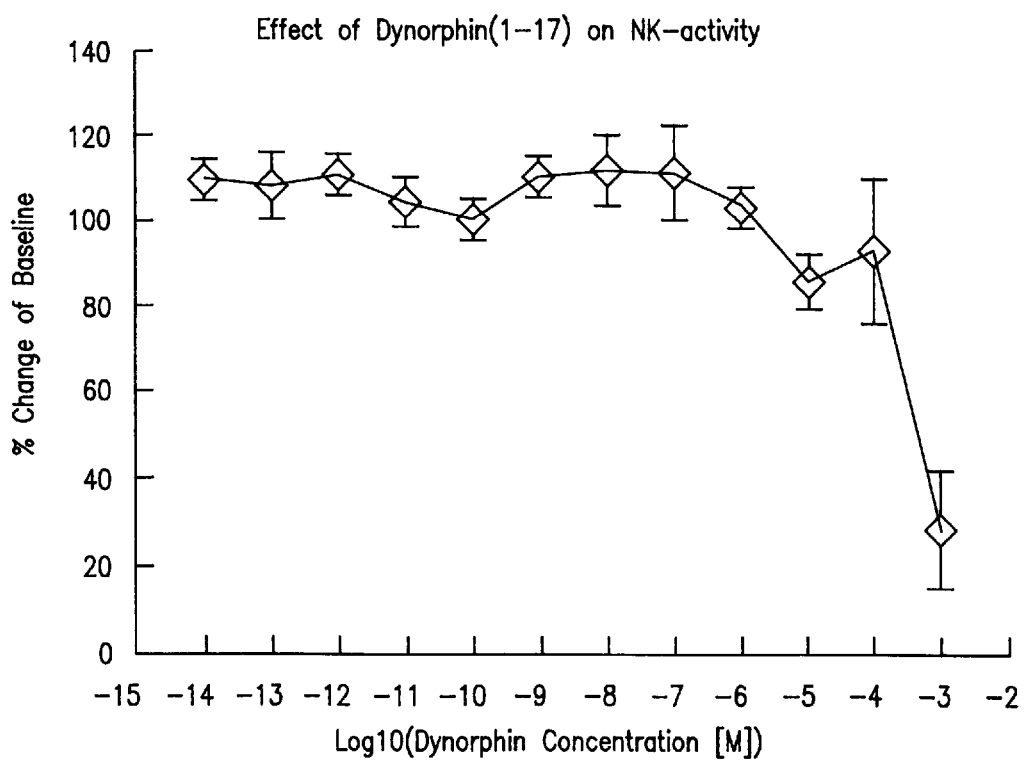

United States Patent [19]
Kreek

[11] Patent Number: 5,817,628
[45] Date of Patent: Oct. 6, 1998

[54] DYNORPHIN A SUPPRESSION OF NATURAL KILLER CELL ACTIVITY

[75] Inventor: Mary Jeanne Kreek, New York, N.Y.

[73] Assignee: The Rockefeller University, New York, N.Y.

[21] Appl. No.: 984,469

[22] Filed: Dec. 2, 1992

[51] Int. Cl.$^6$ .............................. A61K 38/00; C07K 7/08
[52] U.S. Cl. ........................... 514/13; 530/327; 530/328; 514/15
[58] Field of Search ................................... 530/326, 328; 514/17, 15

[56] References Cited

U.S. PATENT DOCUMENTS

| | | | |
|---|---|---|---|
| 4,361,553 | 11/1982 | Loh et al. | 424/177 |
| 4,462,941 | 7/1984 | Lee et al. | 424/177 |
| 4,481,191 | 11/1984 | Wei et al. | 424/177 |
| 4,537,878 | 8/1985 | Plotnikoff et al. | 514/2 |
| 4,684,624 | 8/1987 | Hosobuchi et al. | 514/15 |
| 4,707,468 | 11/1987 | Yoshino et al. | 514/16 |
| 4,757,049 | 7/1988 | Plotnikoff et al. | 514/17 |
| 4,801,614 | 1/1989 | Plotnikoff et al. | 514/17 |
| 5,017,689 | 5/1991 | Hruby et al. | 530/327 |

FOREIGN PATENT DOCUMENTS 9202547   2/1992   WIPO .

OTHER PUBLICATIONS

Oleson, et al.; Brain, Behavior, and Immunity 2:171–186 (1988).
Cseuz, et al.; British Journal of Rheumatology 29:258–362 (1990).
R.M. Silver; Clinical and Experimental Rheumatology 8:481–486 (1990).
Nakamura, et al.; Diabetes, 39:836–843 (1990).
Rose; Clinical Immunology and Immunopathology 53;S7–S16 (1989).
Grunebaum, et al.; Immunol. Res. 8:292–304 (1989).
W.F. Hickey, et al.; J. Exp. Med. 176:811–817 (Sep. 1990).
S.J. Richards; Leukemia and Lymphoma, 7:377–399 (1992).
M.S. Shachner, et al.; Journal of Surgical Research 52:601–604 (1992).
G.F. Solomon; Int. J. Sports Med. 12:S50–S52 (1991).
Prete, et al.; "The In Vitro Effects of Endogenous Opiates on Natural Killer Cells, Antigen–Specific Cytolytic T–Cells, and T–Cell Subsets"; Experimental Neurology, May 1986, vol. 92, No. 2, pp. 349–359.
Prete, et al.; "The Effect of Neuropeptides on Mitogenic Responses, and NK Activity in Systemic Lipus Erythematosus (SLE)". Federation of American Societies for Experimental Biology, 71st Annual Meeting; 29 Mar. 1987, Washington, D.C., Abstract No. 1327, p. 544.
Taylor, et al.; "Peptide Models of Dynorphin A (1–17) Incorporating Minimally Homologous Substitutes for the Potential Amphiphilic Beta Strand in Residues 7–15"; Biochemistry; vol. 29, No. 22, 5 Jun. 1990, pp. 5364–5373.
Hata, Kensaku et al.; "Natural Killer Activity of Human Liver—Derived Lymphocytes in Various Liver Diseases"; Hepatology, Sep. 1991, vol. 14, No. 3, pp. 495–503.

Mulligan, Richard C.; "Gene Transfer And Gene Therapy—Principles, Prospects, and Perspective"; Etiology of Human Disease at the DNA Level, 1991, pp. 143–189.
Oshshorn, Miriam et al.; "In Vitro Studies of the Effect of Methadon on Natural Killer Cell Activity"; Israel Journal of Medical Sciences, Aug. 1990, vol. 26, No. 8, pp. 421–425.
Rosenberg, Steven A., M.D., Ph.D. et al.; "Gene Transfer Into Humans—Immunotherapy Of Patients With Advanced Melanoma, Using Tumor–Infiltrating Lymphocytes Modified By Retroviral Gene Transduction"; The New England Journal of Medicine, Aug. 30, 1990, vol. 323, No. 9, pp. 571–578.
Mary Jeanne Kreek, "Immune Function in Heroin Addicts and Former Heroin Addicts In Treatment: Pre– and Post–AIDS Epidemic", NIDA Research Monograph Series, 1990, vol. 96, pp. 192–219.
Novick, David M. et al.; "Natural Killer Cell Activity and Lymphocyte Subsets in Parenteral Heroin Abusers and Long–term Methadone Maintenance Patients"; The Journal of Pharmacology and Experimental Therapeutics, Aug. 1989, vol. 250, No. 2, pp. 606–610.
Smith, Andrew P. and Nancy M. Lee,; "Pharmacology Of Dynorphin"; Annual Review of Pharmacology and Toxicology, 1988, vol. 28, pp. 123–140.
Sibinga, Nicholas E.S. and Avram Goldstein; "Opioid Peptides And Opioid Receptors In Cells Of The Immune System"; Annual Review of Immunology, 1988, vol. 6, pp. 219–249.
Mandler, Raul N. et al.; "β–Endorphin Augments The Cytolytic Activity and Interferon Production of Natural Killer Cells"; 1986, The Journal of Immunology, vol. 136, No. 3, pp. 934–939.
Joseph Wybran; "Enkephalins and Endorphins As Modifiers of the Immune System: Present and Future"; Federation Proceedings, Jan. 1985, vol. 44, No. 1, pp. 92–94.
Kay, Neil et al.; "Endorphins Stimulate Normal Human Peripheral Blood Lymphocyte Natural Killer Activity"; Life Sciences, 1984 vol. 35, pp. 53–59.

(List continued on next page.)

*Primary Examiner*—Cecilia J. Tsang
*Assistant Examiner*—S. G. Marshall
*Attorney, Agent, or Firm*—Morgan & Finnegan,L.L.P.

[57] ABSTRACT

This invention provides a method of suppressing the cytotoxic activity of mammalian Natural Killer (NK) cells.

The method of this invention comprises administering to an individual in need of treatment a polypeptide comprising the amino acid sequence corresponding to dynorphin A or a dynorphin A analog, including amidated analogs, in an amount sufficient to suppress the cytotoxic activity of NK cells. This invention is particularly useful for those individuals undergoing gene therapy who are to be infected with a viral or viroid vector containing a therapeutic gene. This invention is also useful to aid recipients of transplanted tissue and for individuals suffering from autoimmune diseases.

18 Claims, 3 Drawing Sheets

OTHER PUBLICATIONS

Faith, Robert E. et al.; "Neuroimmunomodulation with Enkephalins: Enhancement of Human Natural Killer (NK) Cell Activity in Vitro"; Clinical Immunology and Immunopathology, 1984, vol. 31, pp. 412–418.

Jen, M.F. et al.; "Dynorphin-(1–13): The Effect Of In Vivo Treatment On Opiate Bindings In Vitro"; European Journal of Pharmacology, 1983, vol. 91, pp. 95–99.

Mathews, Paul M. et al.; "Enhancement of Natural Cytotoxicity By β–Endorphin", The Journal of Immunology, Apr. 1983, vol. 130, No. 4, pp. 1658–1662.

Chavkin, Charles et al.; "Dynorphin Is a Specific Endogenous Ligand of the κ Opioid Receptor"; Science; Jan. 22, 1982, vol. 215, No. 4531, pp. 413–415.

Laidlow, Stewart A. and Kivie Moldave; "The Effects of β–Endorphin and Enkephalins on Protein Biosynthesis in a Eurkaryotic Cell–Free System", The Journal of Biological Chemistry, Dec. 1980, vol. 255, No. 24, pp. 11908–11913.

Goldstein, Avram et al.; "Dyhorphin–(1–13), An Extraordinarily Potent Opioid Peptide," Proceedings of the National Academy of Sciences, Dec. 1979, vol. 76, No. 12, pp. 6666–6670.

Mary Jeanne Kreek, "Medical Complications In Methadone Patients", Annals of The New York Academy of Sciences, 1978, vol. 311, pp. 110–134.

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 10 amino acids
        ( B ) TYPE: Amino Acid
        ( C ) STRANDEDNESS: Single
        ( D ) TOPOLOGY: Unknown ( i i ) MOLECULE TYPE: Peptide ( i x ) FEATURE:
        ( B ) LOCATION: 1
        ( D ) OTHER INFORMATION: Xaa is residue of Tyr, m-Tyr, or
            Dihydroxyphenylalanine ( i x ) FEATURE:
        ( B ) LOCATION: 2
        ( D ) OTHER INFORMATION: Xaa is residue of Gly, Ser, Thr,
            Cys, Tyr, Asn, Gln, or Aib ( i x ) FEATURE:
        ( B ) LOCATION: 3
        ( D ) OTHER INFORMATION: Xaa is residue of Gly, Ser, Thr,
            Cys, Tyr, Asn, Gln, or Aib ( i x ) FEATURE:
        ( B ) LOCATION: 4
        ( D ) OTHER INFORMATION: Xaa is residue of Phe,
            Alpha- alkylated Phe, Alpha-methyl Phe, Tyr, Phe wherein
            the phenyl ring is para-substituted electron with an
            electron withdrawing group such as a halogen or nitro
            group ( i x ) FEATURE:
        ( B ) LOCATION: 5

( D ) OTHER INFORMATION: Xaa is residue of Leu, Ile, Val,
Pro, Phe, Trp or Met ( i x ) FEATURE:
( B ) LOCATION: 6
( D ) OTHER INFORMATION: Xaa is residue of Arg, Lys, His,
Orn, or Homoarginine ( i x ) FEATURE:
( B ) LOCATION: 7
( D ) OTHER INFORMATION: Xaa is residue of Arg, Lys, His,
Orn, or Homoarginine ( i x ) FEATURE:
( B ) LOCATION: 8
( D ) OTHER INFORMATION: Xaa is residue of Ile, Tyr, Leu
or Lys ( i x ) FEATURE:
( B ) LOCATION: 9
( D ) OTHER INFORMATION: Xaa is residue of Arg, Lys, His,
Orn, Pro, or Homoarginine ( i x ) FEATURE:
( B ) LOCATION: 10
( D ) OTHER INFORMATION: Xaa is residue of the amide form of
Pro, Thioproline, 4Hyp,
Pipecolic Acid or 3,4-dehyroproline; or a substituted
amide wherein one or both hydrogens of the amide
nitrogen are C1-4 alkyl, an optionally substituted
benzylic group; or one of the amide hydrogens is a
nitrogen containing moiety such as hydrazide.

( x i ) SEQUENCE DESCRIPTION:SEQ ID NO: 1:

Xaa Xaa Xaa Xaa Xaa Xaa Xaa Xaa Xaa Xaa
1               5                       1 0

( 2 ) INFORMATION FOR SEQ ID NO:2:

( i ) SEQUENCE CHARACTERISTICS:
( A ) LENGTH: 11 amino acids
( B ) TYPE: Amino Acid
( C ) STRANDEDNESS: Single
( D ) TOPOLOGY: Unknown ( i i ) MOLECULE TYPE: Peptide ( i x ) FEATURE:
( B ) LOCATION: 1
( D ) OTHER INFORMATION: Xaa is residue of Tyr, m-Tyr, or
Dihydroxyphenylalanine ( i x ) FEATURE:
( B ) LOCATION: 2
( D ) OTHER INFORMATION: Xaa is residue of Gly, Ser, Thr,
Cys, Tyr, Asn, Gln, or Aib ( i x ) FEATURE:
( B ) LOCATION: 3
( D ) OTHER INFORMATION: Xaa is residue of Gly, Ser, Thr,
Cys, Tyr, Asn, Gln, or Aib ( i x ) FEATURE:
( B ) LOCATION: 4
( D ) OTHER INFORMATION: Xaa is residue of Phe,
Alpha- alkylated Phe, Alpha-methyl Phe, Tyr, Phe wherein
the phenyl ring is para-substituted electron with an
electron withdrawing group such as a halogen or nitro
group ( i x ) FEATURE:
( B ) LOCATION: 5
( D ) OTHER INFORMATION: Xaa is residue of Leu, Ile, Val,
Pro, Phe, Trp or Met ( i x ) FEATURE:
( B ) LOCATION: 6
( D ) OTHER INFORMATION: Xaa is residue of Arg, Lys, His, Orn, or Homoarginine (ix) FEATURE:
    (B) LOCATION: 7
    (D) OTHER INFORMATION: Xaa is residue of Arg, Lys, His,
        Orn, or Homoarginine (ix) FEATURE:
    (B) LOCATION: 8
    (D) OTHER INFORMATION: Xaa is residue of Ile, Tyr, Leu
        or Lys (ix) FEATURE:
    (B) LOCATION: 9
    (D) OTHER INFORMATION: Xaa is residue of Arg, Lys, His,
        Orn, Pro, or Homoarginine (ix) FEATURE:
    (B) LOCATION: 10
    (D) OTHER INFORMATION: Xaa is residue of Pro, Thioproline,
        4Hyp, Pipecolic Acid or 3,4-dehyroproline (ix) FEATURE:
    (B) LOCATION: 11
    (D) OTHER INFORMATION: Xaa is residue of the amide form of
        Arg, Lys, His, Orn, or Homoarginine; or a substituted
        amide wherein one or both hydrogens of the amide
        nitrogen are C1-4 alkyl, an optionally substituted
        benzylic group; or one of the amide hydrogens is a
        nitrogen containing moiety such as hydrazide.

(xi) SEQUENCE DESCRIPTION:SEQ ID NO: 2:

Xaa Xaa Xaa Xaa Xaa Xaa Xaa Xaa Xaa Xaa Xaa
1                     5                              10

(2) INFORMATION FOR SEQ ID NO:3:

(i) SEQUENCE CHARACTERISTICS:
        (A) LENGTH: 12 amino acids
        (B) TYPE: Amino Acid
        (C) STRANDEDNESS: Single
        (D) TOPOLOGY: Unknown (ii) MOLECULE TYPE: Peptide (ix) FEATURE:
        (B) LOCATION: 1
        (D) OTHER INFORMATION: Xaa is residue of Tyr, m-Tyr, or
            Dihydroxyphenylalanine (ix) FEATURE:
        (B) LOCATION: 2
        (D) OTHER INFORMATION: Xaa is residue of Gly, Ser, Thr,
            Cys, Tyr, Asn, Gln, or Aib (ix) FEATURE:
        (B) LOCATION: 3
        (D) OTHER INFORMATION: Xaa is residue of Gly, Ser, Thr,
            Cys, Tyr, Asn, Gln, or Aib (ix) FEATURE:
        (B) LOCATION: 4
        (D) OTHER INFORMATION: Xaa is residue of Phe,
            Alpha- alkylated Phe, Alpha-methyl Phe, Tyr, Phe wherein
            the phenyl ring is para-substituted electron with an
            electron withdrawing group such as a halogen or nitro
            group (ix) FEATURE:
        (B) LOCATION: 5
        (D) OTHER INFORMATION: Xaa is residue of Leu, Ile, Val,
            Pro, Phe, Trp or Met (ix) FEATURE:
        (B) LOCATION: 6
        (D) OTHER INFORMATION: Xaa is residue of Arg, Lys, His,
            Orn, or Homoarginine ( i x ) FEATURE:
    ( B ) LOCATION: 7
    ( D ) OTHER INFORMATION: Xaa is residue of Arg, Lys, His,
        Orn, or Homoarginine ( i x ) FEATURE:
    ( B ) LOCATION: 8
    ( D ) OTHER INFORMATION: Xaa is residue of Ile, Tyr, Leu
        or Lys ( i x ) FEATURE:
    ( B ) LOCATION: 9
    ( D ) OTHER INFORMATION: Xaa is residue of Arg, Lys, His,
        Orn, Pro, or Homoarginine ( i x ) FEATURE:
    ( B ) LOCATION: 10
    ( D ) OTHER INFORMATION: Xaa is residue of Pro, Thioproline,
        4Hyp, Pipecolic Acid or 3,4-dehyroproline ( i x ) FEATURE:
    ( B ) LOCATION: 11
    ( D ) OTHER INFORMATION: Xaa is residue of Arg, Lys, His,
        Orn, or Homoarginine ( i x ) FEATURE:
    ( B ) LOCATION: 12
    ( D ) OTHER INFORMATION: Xaa is residue of the amide form of
        Ile, Tyr, Leu or Lys; or a substituted
        amide wherein one or both hydrogens of the amide
        nitrogen are C1-4 alkyl, an optionally substituted
        benzylic group; or one of the amide hydrogens is a
        nitrogen containing moiety such as hydrazide.

( x i ) SEQUENCE DESCRIPTION:SEQ ID NO: 3:

Xaa Xaa Xaa Xaa Xaa Xaa Xaa Xaa Xaa Xaa Xaa Xaa
1                        5                          10

( 2 ) INFORMATION FOR SEQ ID NO:4:

( i ) SEQUENCE CHARACTERISTICS:
        ( A ) LENGTH: 13 amino acids
        ( B ) TYPE: Amino Acid
        ( C ) STRANDEDNESS: Single
        ( D ) TOPOLOGY: Unknown ( i i ) MOLECULE TYPE: Peptide ( i x ) FEATURE:
        ( B ) LOCATION: 1
        ( D ) OTHER INFORMATION: Xaa is residue of Tyr, m-Tyr, or
            Dihydroxyphenylalanine ( i x ) FEATURE:
        ( B ) LOCATION: 2
        ( D ) OTHER INFORMATION: Xaa is residue of Gly, Ser, Thr,
            Cys, Tyr, Asn, Gln, or Aib ( i x ) FEATURE:
        ( B ) LOCATION: 3
        ( D ) OTHER INFORMATION: Xaa is residue of Gly, Ser, Thr,
            Cys, Tyr, Asn, Gln, or Aib ( i x ) FEATURE:
        ( B ) LOCATION: 4
        ( D ) OTHER INFORMATION: Xaa is residue of Phe,
            Alpha- alkylated Phe, Alpha-methyl Phe, Tyr, Phe wherein
            the phenyl ring is para-substituted electron with an
            electron withdrawing group such as a halogen or nitro
            group ( i x ) FEATURE:
        ( B ) LOCATION: 5
        ( D ) OTHER INFORMATION: Xaa is residue of Leu, Ile, Val,
            Pro, Phe, Trp or Met ( i x ) FEATURE:
        ( B ) LOCATION: 6

(D) OTHER INFORMATION: Xaa is residue of Arg, Lys, His, Orn, or Homoarginine (ix) FEATURE:
(B) LOCATION: 7
(D) OTHER INFORMATION: Xaa is residue of Arg, Lys, His, Orn, or Homoarginine (ix) FEATURE:
(B) LOCATION: 8
(D) OTHER INFORMATION: Xaa is residue of Ile, Tyr, Leu or Lys (ix) FEATURE:
(B) LOCATION: 9
(D) OTHER INFORMATION: Xaa is residue of Arg, Lys, His, Orn, Pro, or Homoarginine (ix) FEATURE:
(B) LOCATION: 10
(D) OTHER INFORMATION: Xaa is residue of Pro, Thioproline, 4Hyp, Pipecolic Acid or 3,4-dehyroproline (ix) FEATURE:
(B) LOCATION: 11
(D) OTHER INFORMATION: Xaa is residue of Arg, Lys, His, Orn, or Homoarginine (ix) FEATURE:
(B) LOCATION: 12
(D) OTHER INFORMATION: Xaa is residue of Ile, Tyr, Leu or Lys (ix) FEATURE:
(B) LOCATION: 13
(D) OTHER INFORMATION: Xaa is residue of the amide form of Arg, Lys, His, Orn, or Homoarginine; or a substituted amide wherein one or both hydrogens of the amide nitrogen are C1-4 alkyl, an optionally substituted benzylic group; or one of the amide hydrogens is a nitrogen containing moiety such as hydrazide.

(xi) SEQUENCE DESCRIPTION:SEQ ID NO: 4:

Xaa Xaa Xaa Xaa Xaa Xaa Xaa Xaa Xaa Xaa Xaa Xaa Xaa
1               5                       10

(2) INFORMATION FOR SEQ ID NO:5:

(i) SEQUENCE CHARACTERISTICS:
(A) LENGTH: 14 amino acids
(B) TYPE: Amino Acid
(C) STRANDEDNESS: Single
(D) TOPOLOGY: Unknown (ii) MOLECULE TYPE: Peptide (ix) FEATURE:
(B) LOCATION: 1
(D) OTHER INFORMATION: Xaa is residue of Tyr, m-Tyr, or Dihydroxyphenylalanine (ix) FEATURE:
(B) LOCATION: 2
(D) OTHER INFORMATION: Xaa is residue of Gly, Ser, Thr, Cys, Tyr, Asn, Gln, or Aib (ix) FEATURE:
(B) LOCATION: 3
(D) OTHER INFORMATION: Xaa is residue of Gly, Ser, Thr, Cys, Tyr, Asn, Gln, or Aib (ix) FEATURE:
(B) LOCATION: 4
(D) OTHER INFORMATION: Xaa is residue of Phe, Alpha- alkylated Phe, Alpha-methyl Phe, Tyr, Phe wherein the phenyl ring is para-substituted electron with an electron withdrawing group such as a halogen or nitro group (ix) FEATURE:
    (B) LOCATION: 5
    (D) OTHER INFORMATION: Xaa is residue of Leu, Ile, Val, Pro, Phe, Trp or Met (ix) FEATURE:
    (B) LOCATION: 6
    (D) OTHER INFORMATION: Xaa is residue of Arg, Lys, His, Orn, or Homoarginine (ix) FEATURE:
    (B) LOCATION: 7
    (D) OTHER INFORMATION: Xaa is residue of Arg, Lys, His, Orn, or Homoarginine (ix) FEATURE:
    (B) LOCATION: 8
    (D) OTHER INFORMATION: Xaa is residue of Ile, Tyr, Leu or Lys (ix) FEATURE:
    (B) LOCATION: 9
    (D) OTHER INFORMATION: Xaa is residue of Arg, Lys, His, Orn, Pro, or Homoarginine (ix) FEATURE:
    (B) LOCATION: 10
    (D) OTHER INFORMATION: Xaa is residue of Pro, Thioproline, 4Hyp, Pipecolic Acid or 3,4-dehyroproline (ix) FEATURE:
    (B) LOCATION: 11
    (D) OTHER INFORMATION: Xaa is residue of Arg, Lys, His, Orn, or Homoarginine (ix) FEATURE:
    (B) LOCATION: 12
    (D) OTHER INFORMATION: Xaa is residue of Ile, Tyr, Leu or Lys (ix) FEATURE:
    (B) LOCATION: 13
    (D) OTHER INFORMATION: Xaa is residue of Arg, Lys, His, Orn, or Homoarginine (ix) FEATURE:
    (B) LOCATION: 14
    (D) OTHER INFORMATION: Xaa is residue of the amide form of Leu, Ile, Val, Pro, Phe, Try or Met; or a substituted amide wherein one or both hydrogens of the amide nitrogen are C1-4 alkyl, an optionally substituted benzylic group; or one of the amide hydrogens is a nitrogen containing moiety such as hydrazide.

(xi) SEQUENCE DESCRIPTION:SEQ ID NO: 5:

Xaa Xaa Xaa Xaa Xaa Xaa Xaa Xaa Xaa Xaa Xaa Xaa Xaa Xaa
1                   5                       10

(2) INFORMATION FOR SEQ ID NO:6:

(i) SEQUENCE CHARACTERISTICS:
        (A) LENGTH: 15 amino acids
        (B) TYPE: Amino Acid
        (C) STRANDEDNESS: Single
        (D) TOPOLOGY: Unknown (ii) MOLECULE TYPE: Peptide (ix) FEATURE:
        (B) LOCATION: 1
        (D) OTHER INFORMATION: Xaa is residue of Tyr, m-Tyr, or Dihydroxyphenylalanine (ix) FEATURE:
        (B) LOCATION: 2
        (D) OTHER INFORMATION: Xaa is residue of Gly, Ser, Thr, Cys, Tyr, Asn, Gln, or Aib ( i x ) FEATURE:
    ( B ) LOCATION: 3
    ( D ) OTHER INFORMATION: Xaa is residue of Gly, Ser, Thr,
        Cys, Tyr, Asn, Gln, or Aib ( i x ) FEATURE:
    ( B ) LOCATION: 4
    ( D ) OTHER INFORMATION: Xaa is residue of Phe,
        Alpha- alkylated Phe, Alpha-methyl Phe, Tyr, Phe wherein
        the phenyl ring is para-substituted electron with an
        electron withdrawing group such as a halogen or nitro
        group ( i x ) FEATURE:
    ( B ) LOCATION: 5
    ( D ) OTHER INFORMATION: Xaa is residue of Leu, Ile, Val,
        Pro, Phe, Trp or Met ( i x ) FEATURE:
    ( B ) LOCATION: 6
    ( D ) OTHER INFORMATION: Xaa is residue of Arg, Lys, His,
        Orn, or Homoarginine ( i x ) FEATURE:
    ( B ) LOCATION: 7
    ( D ) OTHER INFORMATION: Xaa is residue of Arg, Lys, His,
        Orn, or Homoarginine ( i x ) FEATURE:
    ( B ) LOCATION: 8
    ( D ) OTHER INFORMATION: Xaa is residue of Ile, Tyr, Leu
        or Lys ( i x ) FEATURE:
    ( B ) LOCATION: 9
    ( D ) OTHER INFORMATION: Xaa is residue of Arg, Lys, His,
        Orn, Pro, or Homoarginine ( i x ) FEATURE:
    ( B ) LOCATION: 10
    ( D ) OTHER INFORMATION: Xaa is residue of Pro, Thioproline,
        4Hyp, Pipecolic Acid or 3,4-dehyroproline ( i x ) FEATURE:
    ( B ) LOCATION: 11
    ( D ) OTHER INFORMATION: Xaa is residue of Arg, Lys, His,
        Orn, or Homoarginine ( i x ) FEATURE:
    ( B ) LOCATION: 12
    ( D ) OTHER INFORMATION: Xaa is residue of Ile, Tyr, Leu or
        Lys ( i x ) FEATURE:
    ( B ) LOCATION: 13
    ( D ) OTHER INFORMATION: Xaa is residue of Arg, Lys, His,
        Orn, or Homoarginine ( i x ) FEATURE:
    ( B ) LOCATION: 14
    ( D ) OTHER INFORMATION: Xaa is residue of Ile, Val,
        Pro, Phe, Trp or Met ( i x ) FEATURE:
    ( B ) LOCATION: 15
    ( D ) OTHER INFORMATION: Xaa is residue of the amide form of
        Gly, Ser, Thr, Cys, Tyr, Asn, Gln, or Aib; or a
        substituted amide wherein one or both hydrogens of the
        amide nitrogen are C1-4 alkyl, an optionally substituted
        benzylic group; or one of the amide hydrogens is a
        nitrogen containing moiety such as hydrazide.

( x i ) SEQUENCE DESCRIPTION:SEQ ID NO: 6:

Xaa Xaa Xaa Xaa Xaa Xaa Xaa Xaa Xaa Xaa Xaa Xaa Xaa Xaa
    1                    5                                10

Xaa
    15

( 2 ) INFORMATION FOR SEQ ID NO:7:

( i ) SEQUENCE CHARACTERISTICS:
        ( A ) LENGTH: 16 amino acids
        ( B ) TYPE: Amino Acid
        ( C ) STRANDEDNESS: Single
        ( D ) TOPOLOGY: Unknown ( i i ) MOLECULE TYPE: Peptide ( i x ) FEATURE:
        ( B ) LOCATION: 1
        ( D ) OTHER INFORMATION: Xaa is residue of Tyr, m-Tyr, or
            Dihydroxyphenylalanine ( i x ) FEATURE:
        ( B ) LOCATION: 2
        ( D ) OTHER INFORMATION: Xaa is residue of Gly, Ser, Thr,
            Cys, Tyr, Asn, Gln, or Aib ( i x ) FEATURE:
        ( B ) LOCATION: 3
        ( D ) OTHER INFORMATION: Xaa is residue of Gly, Ser, Thr,
            Cys, Tyr, Asn, Gln, or Aib ( i x ) FEATURE:
        ( B ) LOCATION: 4
        ( D ) OTHER INFORMATION: Xaa is residue of Phe,
            Alpha- alkylated Phe, Alpha-methyl Phe, Tyr, Phe wherein
            the phenyl ring is para-substituted electron with an
            electron withdrawing group such as a halogen or nitro
            group ( i x ) FEATURE:
        ( B ) LOCATION: 5
        ( D ) OTHER INFORMATION: Xaa is residue of Leu, Ile, Val,
            Pro, Phe, Trp or Met ( i x ) FEATURE:
        ( B ) LOCATION: 6
        ( D ) OTHER INFORMATION: Xaa is residue of Arg, Lys, His,
            Orn, or Homoarginine ( i x ) FEATURE:
        ( B ) LOCATION: 7
        ( D ) OTHER INFORMATION: Xaa is residue of Arg, Lys, His,
            Orn, or Homoarginine ( i x ) FEATURE:
        ( B ) LOCATION: 8
        ( D ) OTHER INFORMATION: Xaa is residue of Ile, Tyr, Leu
            or Lys ( i x ) FEATURE:
        ( B ) LOCATION: 9
        ( D ) OTHER INFORMATION: Xaa is residue of Arg, Lys, His,
            Orn, Pro, or Homoarginine ( i x ) FEATURE:
        ( B ) LOCATION: 10
        ( D ) OTHER INFORMATION: Xaa is residue of Pro, Thioproline,
            4Hyp, Pipecolic Acid or 3,4-dehyroproline ( i x ) FEATURE:
        ( B ) LOCATION: 11
        ( D ) OTHER INFORMATION: Xaa is residue of Arg, Lys, His,
            Orn, or Homoarginine ( i x ) FEATURE:
        ( B ) LOCATION: 12
        ( D ) OTHER INFORMATION: Xaa is residue of Ile, Tyr, Leu or
            Lys ( i x ) FEATURE:
        ( B ) LOCATION: 13
        ( D ) OTHER INFORMATION: Xaa is residue of Arg, Lys, His,
            Orn, or Homoarginine ( i x ) FEATURE:
  ( B ) LOCATION: 14
  ( D ) OTHER INFORMATION: Xaa is residue of Leu, Ile, Val,
    Pro, Phe, Try or Met ( i x ) FEATURE:
  ( B ) LOCATION: 15
  ( D ) OTHER INFORMATION: Xaa is residue of Gly, Ser, Thr,
    Cys, Tyr, Asn, Gln, or Aib ( i x ) FEATURE:
  ( B ) LOCATION: 16
  ( D ) OTHER INFORMATION: Xaa is residue of the amide form of
    Gly, Ser, Thr, Cys, Tyr, Asn, Gln, or Aib; or a
    substituted amide wherein one or both hydrogens of the
    amide nitrogen are C1-4 alkyl, an optionally substituted
    benzylic group; or one of the amide hydrogens is a
    nitrogen containing moiety such as hydrazide.

( x i ) SEQUENCE DESCRIPTION:SEQ ID NO: 7:

```
Xaa  Xaa  Xaa  Xaa  Xaa  Xaa  Xaa  Xaa  Xaa  Xaa  Xaa  Xaa  Xaa  Xaa
1                  5                             10
Xaa  Xaa
15
```

( 2 ) INFORMATION FOR SEQ ID NO:8:

( i ) SEQUENCE CHARACTERISTICS:
  ( A ) LENGTH: 17 amino acids
  ( B ) TYPE: Amino Acid
  ( C ) STRANDEDNESS: Single
  ( D ) TOPOLOGY: Unknown ( i i ) MOLECULE TYPE: Peptide ( i x ) FEATURE:
  ( B ) LOCATION: 1
  ( D ) OTHER INFORMATION: Xaa is residue of Tyr, m-Tyr, or
    Dihydroxyphenylalanine ( i x ) FEATURE:
  ( B ) LOCATION: 2
  ( D ) OTHER INFORMATION: Xaa is residue of Gly, Ser, Thr,
    Cys, Tyr, Asn, Gln, or Aib ( i x ) FEATURE:
  ( B ) LOCATION: 3
  ( D ) OTHER INFORMATION: Xaa is residue of Gly, Ser, Thr,
    Cys, Tyr, Asn, Gln, or Aib ( i x ) FEATURE:
  ( B ) LOCATION: 4
  ( D ) OTHER INFORMATION: Xaa is residue of Phe,
    Alpha- alkylated Phe, Alpha-methyl Phe, Tyr, Phe wherein
    the phenyl ring is para-substituted electron with an
    electron withdrawing group such as a halogen or nitro
    group ( i x ) FEATURE:
  ( B ) LOCATION: 5
  ( D ) OTHER INFORMATION: Xaa is residue of Leu, Ile, Val,
    Pro, Phe, Trp or Met ( i x ) FEATURE:
  ( B ) LOCATION: 6
  ( D ) OTHER INFORMATION: Xaa is residue of Arg, Lys, His,
    Orn, or Homoarginine ( i x ) FEATURE:
  ( B ) LOCATION: 7
  ( D ) OTHER INFORMATION: Xaa is residue of Arg, Lys, His,
    Orn, or Homoarginine ( i x ) FEATURE:
  ( B ) LOCATION: 8
  ( D ) OTHER INFORMATION: Xaa is residue of Ile, Tyr, Leu
    or Lys ( i x ) FEATURE:
    ( B ) LOCATION: 9
    ( D ) OTHER INFORMATION: Xaa is residue of Arg, Lys, His,
        Orn, Pro, or Homoarginine ( i x ) FEATURE:
    ( B ) LOCATION: 10
    ( D ) OTHER INFORMATION: Xaa is residue of Pro, Thioproline,
        4Hyp, Pipecolic Acid or 3,4-dehyroproline ( i x ) FEATURE:
    ( B ) LOCATION: 11
    ( D ) OTHER INFORMATION: Xaa is residue of Arg, Lys, His,
        Orn, or Homoarginine ( i x ) FEATURE:
    ( B ) LOCATION: 12
    ( D ) OTHER INFORMATION: Xaa is residue of Ile, Tyr, Leu or
        Lys ( i x ) FEATURE:
    ( B ) LOCATION: 13
    ( D ) OTHER INFORMATION: Xaa is residue of Arg, Lys, His,
        Orn, or Homoarginine ( i x ) FEATURE:
    ( B ) LOCATION: 14
    ( D ) OTHER INFORMATION: Xaa is residue of Leu, Ile, Val,
        Pro, Phe, Try or Met ( i x ) FEATURE:
    ( B ) LOCATION: 15
    ( D ) OTHER INFORMATION: Xaa is residue of Gly, Ser, Thr,
        Cys, Tyr, Asn, Gln, or Aib ( i x ) FEATURE:
    ( B ) LOCATION: 16
    ( D ) OTHER INFORMATION: Xaa is residue of Gly, Ser, Thr,
        Cys, Tyr, Asn, Gln, or Aib; or a
        substituted amide wherein one or both hydrogens of the
        amide nitrogen are C1-4 alkyl, an optionally substituted
        benzylic group; or one of the amide hydrogens is a
        nitrogen containing moiety such as hydrazide.

( i x ) FEATURE:
    ( B ) LOCATION: 17
    ( D ) OTHER INFORMATION: Xaa is residue of the amide form of
        Gly, Ser, Thr, Cys, Tyr, Asn, Gln, or Aib ( x i ) SEQUENCE DESCRIPTION:SEQ ID NO: 8:

Xaa Xaa Xaa Xaa Xaa Xaa Xaa Xaa Xaa Xaa Xaa Xaa Xaa Xaa
1                    5                          10

Xaa Xaa Xaa
15

( 2 ) INFORMATION FOR SEQ ID NO:9:

( i ) SEQUENCE CHARACTERISTICS:
        ( A ) LENGTH: 10 amino acids
        ( B ) TYPE: Amino Acid
        ( C ) STRANDEDNESS: Single
        ( D ) TOPOLOGY: Unknown ( i i ) MOLECULE TYPE: Peptide ( i x ) FEATURE:
        ( B ) LOCATION: 1
        ( D ) OTHER INFORMATION: Xaa is residue of Tyr, m-Tyr, or
            Dihydroxyphenylalanine ( i x ) FEATURE:
        ( B ) LOCATION: 2
        ( D ) OTHER INFORMATION: Xaa is residue of Gly, Ser, Thr,
            Cys, Tyr, Asn, Gln, or Aib ( i x ) FEATURE:

(B) LOCATION: 3
                (D) OTHER INFORMATION: Xaa is residue of Gly, Ser, Thr,
                        Cys, Tyr, Asn, Gln, or Aib (ix) FEATURE:
                (B) LOCATION: 4
                (D) OTHER INFORMATION: Xaa is residue of Phe,
                        Alpha- alkylated Phe, Alpha-methyl Phe, Tyr, Phe wherein
                        the phenyl ring is para-substituted electron with an
                        electron withdrawing group such as a halogen or nitro
                        group (ix) FEATURE:
                (B) LOCATION: 5
                (D) OTHER INFORMATION: Xaa is residue of Leu, Ile, Val,
                        Pro, Phe, Trp or Met (ix) FEATURE:
                (B) LOCATION: 6
                (D) OTHER INFORMATION: Xaa is residue of Arg, Lys, His,
                        Orn, or Homoarginine (ix) FEATURE:
                (B) LOCATION: 7
                (D) OTHER INFORMATION: Xaa is residue of Arg, Lys, His,
                        Orn, or Homoarginine (ix) FEATURE:
                (B) LOCATION: 8
                (D) OTHER INFORMATION: Xaa is residue of Ile, Tyr, Leu
                        or Lys (ix) FEATURE:
                (B) LOCATION: 9
                (D) OTHER INFORMATION: Xaa is residue of Arg, Lys, His,
                        Orn, Pro, or Homoarginine (ix) FEATURE:
                (B) LOCATION: 10
                (D) OTHER INFORMATION: Xaa is residue of either the
                        carboxyl or amide form of Pro, Thioproline, 4Hyp,
                        Pipecolic Acid or 3,4-dehydroproline (xi) SEQUENCE DESCRIPTION:SEQ ID NO: 9:

Xaa  Xaa  Xaa  Xaa  Xaa  Xaa  Xaa  Xaa  Xaa  Xaa
            1                   5                        10

(2) INFORMATION FOR SEQ ID NO:10:

(i) SEQUENCE CHARACTERISTICS:
                (A) LENGTH: 11 amino acids
                (B) TYPE: Amino Acid
                (C) STRANDEDNESS: Single
                (D) TOPOLOGY: Unknown (ii) MOLECULE TYPE: Peptide (ix) FEATURE:
                (B) LOCATION: 1
                (D) OTHER INFORMATION: Xaa is residue of Tyr, m-Tyr, or
                        Dihydroxyphenylalanine (ix) FEATURE:
                (B) LOCATION: 2
                (D) OTHER INFORMATION: Xaa is residue of Gly, Ser, Thr,
                        Cys, Tyr, Asn, Gln, or Aib (ix) FEATURE:
                (B) LOCATION: 3
                (D) OTHER INFORMATION: Xaa is residue of Gly, Ser, Thr,
                        Cys, Tyr, Asn, Gln, or Aib (ix) FEATURE:
                (B) LOCATION: 4
                (D) OTHER INFORMATION: Xaa is residue of Phe,
                        Alpha- alkylated Phe, Alpha-methyl Phe, Tyr, Phe wherein
                        the phenyl ring is para-substituted electron with an
                        electron withdrawing group such as a halogen or nitro group (ix) FEATURE:
    (B) LOCATION: 5
    (D) OTHER INFORMATION: Xaa is residue of Leu, Ile, Val,
        Pro, Phe, Trp or Met (ix) FEATURE:
    (B) LOCATION: 6
    (D) OTHER INFORMATION: Xaa is residue of Arg, Lys, His,
        Orn, or Homoarginine (ix) FEATURE:
    (B) LOCATION: 7
    (D) OTHER INFORMATION: Xaa is residue of Arg, Lys, His,
        Orn, or Homoarginine (ix) FEATURE:
    (B) LOCATION: 8
    (D) OTHER INFORMATION: Xaa is residue of Ile, Tyr, Leu
        or Lys (ix) FEATURE:
    (B) LOCATION: 9
    (D) OTHER INFORMATION: Xaa is residue of Arg, Lys, His,
        Orn, Pro, or Homoarginine (ix) FEATURE:
    (B) LOCATION: 10
    (D) OTHER INFORMATION: Xaa is residue of Pro, Thioproline,
        4Hyp, Pipecolic Acid or 3,4-dehyroproline (ix) FEATURE:
    (B) LOCATION: 11
    (D) OTHER INFORMATION: Xaa is residue of either the
        carboxyl or amide form of Arg, Lys, His, Orn, or
        Homoarginine (xi) SEQUENCE DESCRIPTION:SEQ ID NO: 10:

Xaa Xaa Xaa Xaa Xaa Xaa Xaa Xaa Xaa Xaa Xaa
    1                   5                       10

(2) INFORMATION FOR SEQ ID NO:11:

(i) SEQUENCE CHARACTERISTICS:
        (A) LENGTH: 12 amino acids
        (B) TYPE: Amino Acid
        (C) STRANDEDNESS: Single
        (D) TOPOLOGY: Unknown (ii) MOLECULE TYPE: Peptide (ix) FEATURE:
        (B) LOCATION: 1
        (D) OTHER INFORMATION: Xaa is residue of Tyr, m-Tyr, or
            Dihydroxyphenylalanine (ix) FEATURE:
        (B) LOCATION: 2
        (D) OTHER INFORMATION: Xaa is residue of Gly, Ser, Thr,
            Cys, Tyr, Asn, Gln, or Aib (ix) FEATURE:
        (B) LOCATION: 3
        (D) OTHER INFORMATION: Xaa is residue of Gly, Ser, Thr,
            Cys, Tyr, Asn, Gln, or Aib (ix) FEATURE:
        (B) LOCATION: 4
        (D) OTHER INFORMATION: Xaa is residue of Phe,
            Alpha- alkylated Phe, Alpha-methyl Phe, Tyr, Phe wherein
            the phenyl ring is para-substituted electron with an
            electron withdrawing group such as a halogen or nitro
            group (ix) FEATURE:
        (B) LOCATION: 5
        (D) OTHER INFORMATION: Xaa is residue of Leu, Ile, Val, Pro, Phe, Trp or Met ( i x ) FEATURE:
    ( B ) LOCATION: 6
    ( D ) OTHER INFORMATION: Xaa is residue of Arg, Lys, His,
        Orn, or Homoarginine ( i x ) FEATURE:
    ( B ) LOCATION: 7
    ( D ) OTHER INFORMATION: Xaa is residue of Arg, Lys, His,
        Orn, or Homoarginine ( i x ) FEATURE:
    ( B ) LOCATION: 8
    ( D ) OTHER INFORMATION: Xaa is residue of Ile, Tyr, Leu
        or Lys ( i x ) FEATURE:
    ( B ) LOCATION: 9
    ( D ) OTHER INFORMATION: Xaa is residue of Arg, Lys, His,
        Orn, Pro, or Homoarginine ( i x ) FEATURE:
    ( B ) LOCATION: 10
    ( D ) OTHER INFORMATION: Xaa is residue of Pro, Thioproline,
        4Hyp, Pipecolic Acid or 3,4-dehyroproline ( i x ) FEATURE:
    ( B ) LOCATION: 11
    ( D ) OTHER INFORMATION: Xaa is residue of Arg, Lys, His,
        Orn, or Homoarginine ( i x ) FEATURE:
    ( B ) LOCATION: 12
    ( D ) OTHER INFORMATION: Xaa is residue of either the
        carboxyl or amide form of Ile, Tyr, Leu or Lys ( x i ) SEQUENCE DESCRIPTION:SEQ ID NO: 11:

```
Xaa  Xaa  Xaa  Xaa  Xaa  Xaa  Xaa  Xaa  Xaa  Xaa  Xaa  Xaa
1                   5                        10
```

( 2 ) INFORMATION FOR SEQ ID NO:12:

( i ) SEQUENCE CHARACTERISTICS:
        ( A ) LENGTH: 13 amino acids
        ( B ) TYPE: Amino Acid
        ( C ) STRANDEDNESS: Single
        ( D ) TOPOLOGY: Unknown ( i i ) MOLECULE TYPE: Peptide ( i x ) FEATURE:
        ( B ) LOCATION: 1
        ( D ) OTHER INFORMATION: Xaa is residue of Tyr, m-Tyr, or
            Dihydroxyphenylalanine ( i x ) FEATURE:
        ( B ) LOCATION: 2
        ( D ) OTHER INFORMATION: Xaa is residue of Gly, Ser, Thr,
            Cys, Tyr, Asn, Gln, or Aib ( i x ) FEATURE:
        ( B ) LOCATION: 3
        ( D ) OTHER INFORMATION: Xaa is residue of Gly, Ser, Thr,
            Cys, Tyr, Asn, Gln, or Aib ( i x ) FEATURE:
        ( B ) LOCATION: 4
        ( D ) OTHER INFORMATION: Xaa is residue of Phe,
            Alpha- alkylated Phe, Alpha-methyl Phe, Tyr, Phe wherein
            the phenyl ring is para-substituted electron with an
            electron withdrawing group such as a halogen or nitro
            group ( i x ) FEATURE:
        ( B ) LOCATION: 5
        ( D ) OTHER INFORMATION: Xaa is residue of Leu, Ile, Val,
            Pro, Phe, Trp or Met ( i x ) FEATURE:
  ( B ) LOCATION: 6
  ( D ) OTHER INFORMATION: Xaa is residue of Arg, Lys, His,
    Orn, or Homoarginine ( i x ) FEATURE:
  ( B ) LOCATION: 7
  ( D ) OTHER INFORMATION: Xaa is residue of Arg, Lys, His,
    Orn, or Homoarginine ( i x ) FEATURE:
  ( B ) LOCATION: 8
  ( D ) OTHER INFORMATION: Xaa is residue of Ile, Tyr, Leu
    or Lys ( i x ) FEATURE:
  ( B ) LOCATION: 9
  ( D ) OTHER INFORMATION: Xaa is residue of Arg, Lys, His,
    Orn, Pro, or Homoarginine ( i x ) FEATURE:
  ( B ) LOCATION: 10
  ( D ) OTHER INFORMATION: Xaa is residue of Pro, Thioproline,
    4Hyp, Pipecolic Acid or 3,4-dehyroproline ( i x ) FEATURE:
  ( B ) LOCATION: 11
  ( D ) OTHER INFORMATION: Xaa is residue of Arg, Lys, His,
    Orn, or Homoarginine ( i x ) FEATURE:
  ( B ) LOCATION: 12
  ( D ) OTHER INFORMATION: Xaa is residue of Ile, Tyr, Leu or
    Lys ( i x ) FEATURE:
  ( B ) LOCATION: 13
  ( D ) OTHER INFORMATION: Xaa is residue of either the
    carboxyl or amide form of Arg, Lys, His, Orn, or
    Homoarginine ( x i ) SEQUENCE DESCRIPTION:SEQ ID NO: 12:

Xaa  Xaa  Xaa  Xaa  Xaa  Xaa  Xaa  Xaa  Xaa  Xaa  Xaa  Xaa  Xaa
    1                   5                        10

( 2 ) INFORMATION FOR SEQ ID NO:13:

( i ) SEQUENCE CHARACTERISTICS:
    ( A ) LENGTH: 14 amino acids
    ( B ) TYPE: Amino Acid
    ( C ) STRANDEDNESS: Single
    ( D ) TOPOLOGY: Unknown ( i i ) MOLECULE TYPE: Peptide ( i x ) FEATURE:
    ( B ) LOCATION: 1
    ( D ) OTHER INFORMATION: Xaa is residue of Tyr, m-Tyr, or
      Dihydroxyphenylalanine ( i x ) FEATURE:
    ( B ) LOCATION: 2
    ( D ) OTHER INFORMATION: Xaa is residue of Gly, Ser, Thr,
      Cys, Tyr, Asn, Gln, or Aib ( i x ) FEATURE:
    ( B ) LOCATION: 3
    ( D ) OTHER INFORMATION: Xaa is residue of Gly, Ser, Thr,
      Cys, Tyr, Asn, Gln, or Aib ( i x ) FEATURE:
    ( B ) LOCATION: 4
    ( D ) OTHER INFORMATION: Xaa is residue of Phe,
      Alpha- alkylated Phe, Alpha-methyl Phe, Tyr, Phe wherein
      the phenyl ring is para-substituted electron with an
      electron withdrawing group such as a halogen or nitro
      group ( i x ) FEATURE:
  ( B ) LOCATION: 5
  ( D ) OTHER INFORMATION: Xaa is residue of Leu, Ile, Val,
    Pro, Phe, Trp or Met ( i x ) FEATURE:
  ( B ) LOCATION: 6
  ( D ) OTHER INFORMATION: Xaa is residue of Arg, Lys, His,
    Orn, or Homoarginine ( i x ) FEATURE:
  ( B ) LOCATION: 7
  ( D ) OTHER INFORMATION: Xaa is residue of Arg, Lys, His,
    Orn, or Homoarginine ( i x ) FEATURE:
  ( B ) LOCATION: 8
  ( D ) OTHER INFORMATION: Xaa is residue of Ile, Tyr, Leu
    or Lys ( i x ) FEATURE:
  ( B ) LOCATION: 9
  ( D ) OTHER INFORMATION: Xaa is residue of Arg, Lys, His,
    Orn, Pro, or Homoarginine ( i x ) FEATURE:
  ( B ) LOCATION: 10
  ( D ) OTHER INFORMATION: Xaa is residue of Pro, Thioproline,
    4Hyp, Pipecolic Acid or 3,4-dehyroproline ( i x ) FEATURE:
  ( B ) LOCATION: 11
  ( D ) OTHER INFORMATION: Xaa is residue of Arg, Lys, His,
    Orn, or Homoarginine ( i x ) FEATURE:
  ( B ) LOCATION: 12
  ( D ) OTHER INFORMATION: Xaa is residue of Ile, Tyr, Leu or
    Lys ( i x ) FEATURE:
  ( B ) LOCATION: 13
  ( D ) OTHER INFORMATION: Xaa is residue of Arg, Lys, His,
    Orn, or Homoarginine ( i x ) FEATURE:
  ( B ) LOCATION: 14
  ( D ) OTHER INFORMATION: Xaa is residue of either the
    carboxyl or amide form of Leu, Ile, Val, Pro, Phe, Trp
    or Met ( x i ) SEQUENCE DESCRIPTION:SEQ ID NO: 13:

Xaa Xaa Xaa Xaa Xaa Xaa Xaa Xaa Xaa Xaa Xaa Xaa Xaa Xaa
 1        5             10

( 2 ) INFORMATION FOR SEQ ID NO:14:

( i ) SEQUENCE CHARACTERISTICS:
  ( A ) LENGTH: 15 amino acids
  ( B ) TYPE: Amino Acid
  ( C ) STRANDEDNESS: Single
  ( D ) TOPOLOGY: Unknown ( i i ) MOLECULE TYPE: Peptide ( i x ) FEATURE:
  ( B ) LOCATION: 1
  ( D ) OTHER INFORMATION: Xaa is residue of Tyr, m-Tyr, or
    Dihydroxyphenylalanine ( i x ) FEATURE:
  ( B ) LOCATION: 2
  ( D ) OTHER INFORMATION: Xaa is residue of Gly, Ser, Thr,
    Cys, Tyr, Asn, Gln, or Aib ( i x ) FEATURE:
  ( B ) LOCATION: 3

(D) OTHER INFORMATION: Xaa is residue of Gly, Ser, Thr, Cys, Tyr, Asn, Gln, or Aib (ix) FEATURE:
 (B) LOCATION: 4
 (D) OTHER INFORMATION: Xaa is residue of Phe, Alpha- alkylated Phe, Alpha-methyl Phe, Tyr, Phe wherein the phenyl ring is para-substituted electron with an electron withdrawing group such as a halogen or nitro group (ix) FEATURE:
 (B) LOCATION: 5
 (D) OTHER INFORMATION: Xaa is residue of Leu, Ile, Val, Pro, Phe, Trp or Met (ix) FEATURE:
 (B) LOCATION: 6
 (D) OTHER INFORMATION: Xaa is residue of Arg, Lys, His, Orn, or Homoarginine (ix) FEATURE:
 (B) LOCATION: 7
 (D) OTHER INFORMATION: Xaa is residue of Arg, Lys, His, Orn, or Homoarginine (ix) FEATURE:
 (B) LOCATION: 8
 (D) OTHER INFORMATION: Xaa is residue of Ile, Tyr, Leu or Lys (ix) FEATURE:
 (B) LOCATION: 9
 (D) OTHER INFORMATION: Xaa is residue of Arg, Lys, His, Orn, Pro, or Homoarginine (ix) FEATURE:
 (B) LOCATION: 10
 (D) OTHER INFORMATION: Xaa is residue of Pro, Thioproline, 4Hyp, Pipecolic Acid or 3,4-dehyroproline (ix) FEATURE:
 (B) LOCATION: 11
 (D) OTHER INFORMATION: Xaa is residue of Arg, Lys, His, Orn, or Homoarginine (ix) FEATURE:
 (B) LOCATION: 12
 (D) OTHER INFORMATION: Xaa is residue of Ile, Tyr, Leu or Lys (ix) FEATURE:
 (B) LOCATION: 13
 (D) OTHER INFORMATION: Xaa is residue of Arg, Lys, His, Orn, or Homoarginine (ix) FEATURE:
 (B) LOCATION: 14
 (D) OTHER INFORMATION: Xaa is residue of Leu, Ile, Val, Pro, Phe, Trp or Met (ix) FEATURE:
 (B) LOCATION: 15
 (D) OTHER INFORMATION: Xaa is residue of either the carboxyl or amide form of Gly, Ser, Thr, Cys, Tyr, Asn, Gln, or Aib (xi) SEQUENCE DESCRIPTION:SEQ ID NO: 14:

Xaa Xaa Xaa Xaa Xaa Xaa Xaa Xaa Xaa Xaa Xaa Xaa Xaa Xaa
1               5                               10
Xaa
15

(2) INFORMATION FOR SEQ ID NO:15:

(i) SEQUENCE CHARACTERISTICS:
  (A) LENGTH: 16 amino acids (B) TYPE: Amino Acid
(C) STRANDEDNESS: Single
(D) TOPOLOGY: Unknown (ii) MOLECULE TYPE: Peptide (ix) FEATURE:
(B) LOCATION: 1
(D) OTHER INFORMATION: Xaa is residue of Tyr, m-Tyr, or Dihydroxyphenylalanine (ix) FEATURE:
(B) LOCATION: 2
(D) OTHER INFORMATION: Xaa is residue of Gly, Ser, Thr, Cys, Tyr, Asn, Gln, or Aib (ix) FEATURE:
(B) LOCATION: 3
(D) OTHER INFORMATION: Xaa is residue of Gly, Ser, Thr, Cys, Tyr, Asn, Gln, or Aib (ix) FEATURE:
(B) LOCATION: 4
(D) OTHER INFORMATION: Xaa is residue of Phe, Alpha- alkylated Phe, Alpha-methyl Phe, Tyr, Phe wherein the phenyl ring is para-substituted electron with an electron withdrawing group such as a halogen or nitro group (ix) FEATURE:
(B) LOCATION: 5
(D) OTHER INFORMATION: Xaa is residue of Leu, Ile, Val, Pro, Phe, Trp or Met (ix) FEATURE:
(B) LOCATION: 6
(D) OTHER INFORMATION: Xaa is residue of Arg, Lys, His, Orn, or Homoarginine (ix) FEATURE:
(B) LOCATION: 7
(D) OTHER INFORMATION: Xaa is residue of Arg, Lys, His, Orn, or Homoarginine (ix) FEATURE:
(B) LOCATION: 8
(D) OTHER INFORMATION: Xaa is residue of Ile, Tyr, Leu or Lys (ix) FEATURE:
(B) LOCATION: 9
(D) OTHER INFORMATION: Xaa is residue of Arg, Lys, His, Orn, Pro, or Homoarginine (ix) FEATURE:
(B) LOCATION: 10
(D) OTHER INFORMATION: Xaa is residue of Pro, Thioproline, 4Hyp, Pipecolic Acid or 3,4-dehyroproline (ix) FEATURE:
(B) LOCATION: 11
(D) OTHER INFORMATION: Xaa is residue of Arg, Lys, His, Orn, or Homoarginine (ix) FEATURE:
(B) LOCATION: 12
(D) OTHER INFORMATION: Xaa is residue of Ile, Tyr, Leu or Lys (ix) FEATURE:
(B) LOCATION: 13
(D) OTHER INFORMATION: Xaa is residue of Arg, Lys, His, Orn, or Homoarginine (ix) FEATURE:
(B) LOCATION: 14
(D) OTHER INFORMATION: Xaa is residue of Leu, Ile, Val, Pro, Phe, Try or Met (ix) FEATURE:

(B) LOCATION: 15
(D) OTHER INFORMATION: Xaa is residue of Gly, Ser, Thr,
    Cys, Tyr, Asn, Gln, or Aib (ix) FEATURE:
    (B) LOCATION: 16
    (D) OTHER INFORMATION: Xaa is residue of either the
        carboxyl or amide form of Gly, Ser, Thr, Cys, Tyr, Asn,
        Gln, or Aib (xi) SEQUENCE DESCRIPTION:SEQ ID NO: 15:

Xaa Xaa Xaa Xaa Xaa Xaa Xaa Xaa Xaa Xaa Xaa Xaa Xaa Xaa
1               5                           10

Xaa Xaa
15

(2) INFORMATION FOR SEQ ID NO:16:

(i) SEQUENCE CHARACTERISTICS:
    (A) LENGTH: 17 amino acids
    (B) TYPE: Amino Acid
    (C) STRANDEDNESS: Single
    (D) TOPOLOGY: Unknown (ii) MOLECULE TYPE: Peptide (ix) FEATURE:
    (B) LOCATION: 1
    (D) OTHER INFORMATION: Xaa is residue of Tyr, m-Tyr, or
        Dihydroxyphenylalanine (ix) FEATURE:
    (B) LOCATION: 2
    (D) OTHER INFORMATION: Xaa is residue of Gly, Ser, Thr,
        Cys, Tyr, Asn, Gln, or Aib (ix) FEATURE:
    (B) LOCATION: 3
    (D) OTHER INFORMATION: Xaa is residue of Gly, Ser, Thr,
        Cys, Tyr, Asn, Gln, or Aib (ix) FEATURE:
    (B) LOCATION: 4
    (D) OTHER INFORMATION: Xaa is residue of Phe,
        Alpha- alkylated Phe, Alpha-methyl Phe, Tyr, Phe wherein
        the phenyl ring is para-substituted electron with an
        electron withdrawing group such as a halogen or nitro
        group (ix) FEATURE:
    (B) LOCATION: 5
    (D) OTHER INFORMATION: Xaa is residue of Leu, Ile, Val,
        Pro, Phe, Trp or Met (ix) FEATURE:
    (B) LOCATION: 6
    (D) OTHER INFORMATION: Xaa is residue of Arg, Lys, His,
        Orn, or Homoarginine (ix) FEATURE:
    (B) LOCATION: 7
    (D) OTHER INFORMATION: Xaa is residue of Arg, Lys, His,
        Orn, or Homoarginine (ix) FEATURE:
    (B) LOCATION: 8
    (D) OTHER INFORMATION: Xaa is residue of Ile, Tyr, Leu
        or Lys (ix) FEATURE:
    (B) LOCATION: 9
    (D) OTHER INFORMATION: Xaa is residue of Arg, Lys, His,
        Orn, Pro, or Homoarginine (ix) FEATURE:
    (B) LOCATION: 10
    (D) OTHER INFORMATION: Xaa is residue of Pro, Thioproline, 4Hyp, Pipecolic Acid or 3,4-dehyroproline ( i x ) FEATURE:
        ( B ) LOCATION: 11
        ( D ) OTHER INFORMATION: Xaa is residue of Arg, Lys, His, Orn, or Homoarginine ( i x ) FEATURE:
        ( B ) LOCATION: 12
        ( D ) OTHER INFORMATION: Xaa is residue of Ile, Tyr, Leu or Lys ( i x ) FEATURE:
        ( B ) LOCATION: 13
        ( D ) OTHER INFORMATION: Xaa is residue of Arg, Lys, His, Orn, or Homoarginine ( i x ) FEATURE:
        ( B ) LOCATION: 14
        ( D ) OTHER INFORMATION: Xaa is residue of Leu, Ile, Val, Pro, Phe, Try or Met ( i x ) FEATURE:
        ( B ) LOCATION: 15
        ( D ) OTHER INFORMATION: Xaa is residue of Gly, Ser, Thr, Cys, Tyr, Asn, Gln, or Aib ( i x ) FEATURE:
        ( B ) LOCATION: 16
        ( D ) OTHER INFORMATION: Xaa is residue of Gly, Ser, Thr, Cys, Tyr, Asn, Gln, or Aib ( i x ) FEATURE:
        ( B ) LOCATION: 17
        ( D ) OTHER INFORMATION: Xaa is residue of either the carboxyl or amide form of Gly, Ser, Thr, Cys, Tyr, Asn, Gln, or Aib ( x i ) SEQUENCE DESCRIPTION:SEQ ID NO: 16:

Xaa Xaa Xaa Xaa Xaa Xaa Xaa Xaa Xaa Xaa Xaa Xaa Xaa Xaa
1               5                           10

Xaa Xaa Xaa
15

( 2 ) INFORMATION FOR SEQ ID NO: 17:

( i ) SEQUENCE CHARACTERISTICS:
        ( A ) LENGTH: 17 amino acids
        ( B ) TYPE: Amino Acid
        ( C ) STRANDEDNESS: Single
        ( D ) TOPOLOGY: Unknown ( i i ) MOLECULE TYPE: Peptide ( i x ) SEQUENCE DESCRIPTION: SEQ ID NO:17:

Tyr Gly Gly Phe Leu Arg Arg Ile Arg Pro Lys Leu Lys Trp
1               5                           10

Asp Asn Gln
15

( 2 ) INFORMATION FOR SEQ ID NO: 18:

( i ) SEQUENCE CHARACTERISTICS:
        ( A ) LENGTH: 16 amino acids
        ( B ) TYPE: Amino Acid
        ( C ) STRANDEDNESS: Single
        ( D ) TOPOLOGY: Unknown ( i i ) MOLECULE TYPE: Peptide ( i x ) FEATURE:
        ( D ) OTHER INFORMATION: This peptide is identical to the mature dynorphin A(1-17) of SEQ ID NO: 17 except for the removal of the amino terminal Tyr (ix) SEQUENCE DESCRIPTION: SEQ ID NO:18:

Gly Gly Phe Leu Arg Arg Ile Arg Pro Lys Leu Lys Trp Asp
1               5                   10

Asn Gln
15

(2) INFORMATION FOR SEQ ID NO: 19:

(i) SEQUENCE CHARACTERISTICS:
  (A) LENGTH: 13 amino acids
  (B) TYPE: Amino Acid
  (C) STRANDEDNESS: Single
  (D) TOPOLOGY: Unknown (ii) MOLECULE TYPE: Peptide (ix) SEQUENCE DESCRIPTION: SEQ ID NO:19:

Tyr Gly Gly Phe Leu Arg Arg Ile Arg Pro Lys Leu Lys
1               5                   10

(2) INFORMATION FOR SEQ ID NO: 20:

(i) SEQUENCE CHARACTERISTICS:
  (A) LENGTH: 10 amino acids
  (B) TYPE: Amino Acid
  (C) STRANDEDNESS: Single
  (D) TOPOLOGY: Unknown (ii) MOLECULE TYPE: Peptide (ix) SEQUENCE DESCRIPTION: SEQ ID NO:20:

Tyr Gly Gly Phe Leu Arg Arg Ile Arg Pro
1               5                   10

DYNORPHIN A SUPPRESSION OF NATURAL KILLER CELL ACTIVITY

FIELD OF THE INVENTION

This invention provides a method of regulating an individual's immune system by administering a polypeptide corresponding to the amino acid sequence of dynorphin or a dynorphin analog. The effect of such administration is to suppress the cytoxic activity of Natural Killer (NK) cells of the immune system.

BACKGROUND OF THE INVENTION

The overall activity of the immune system is dependent on the activity of the various component cells that contribute to an immune response.

One type of immune cell, natural killer cells (NK cells), are able to attack and kill cells such as tumor cells and normal cells infected by virus. NK cells play a significant role in the body's rejection of foreign tissue and are also a prominent cell type in lesions associated with graft versus host disease in recipients of bone marrow transplants. In such a disease NK cells from the grafted bone marrow become activated and attack normal host cells.

NK cells are a normal population of large granular lymphocytes comprising about 5% of total lymphocytes. NK cells are found in blood, lymphoid tissue including spleen and are a subset of lymphocytes derived from bone marrow. NK cells are also present in liver as Kupffer cells and in the Peyers patches of the gastrointestinal tract. Because NK cells are migratory they may be found in other tissues as well.

Killing of cells by NK cells is not specific for particular viral antigenic determinants and is not restricted by MHC molecules. The term "cold target inhibition" has been used to describe the phenomenon whereby one NK target cell type can inhibit lysis of a different NK target cell type by competing for effective cells.

Opioid effects on the immune system have recently drawn the attention of several investigators. This attention was initially based on the observation that abusers of heroin had various immunogenic abnormalities such as generalized lymphadenopathy (Helpern and Rho, N.Y. State J. Med. 66:2391–2408, 1966) elevated serum immunoglobulins (Cushman & Grieco, Am. J. Med., 54:320–326, 1973; Kreek et al., Ann. Intern. Med., 77:598–602, 1972), lymphocytosis (Kreek, J. Am. Med. Assoc., 223:665–668, 1973), decreased responses of lymphocytes to mitogens in short term culture (Brown et al., Arch. Intern. Med., 134:1001–1006, 1974) and abnormal T cells rosette formation.

More recently, Novick et al. reported that the activity of NK cells was significantly reduced in parenteral abusers of the short acting opiate heroin compared to healthy individuals and individuals who had been on methadone maintenance and had not abused drugs for at least ten years. Methadone is a long-acting opiate agonist which exhibits cross-tolerance with heroin, a potent and short-acting opiate agonist. Novick et al., J. Pharm. Expt. Ther., 250:606–610, 1989.

Results of experiments concerning the effect of opioids on NK cell activity is conflicting. Improvement in NK activity in stable long term methadone maintenance patients was reported despite the possible existence of direct effects of opioids on some indices of cellular immunity. Novick et al., J. Pharm. Expt. Ther., 250:606–610, 1989; Kreek et al., NIDA Research Monograph Series, 96:192–219, 1990; Ochshorn et al., Isr. J. Med Sci., 26:421–425, 1990. Direct effect of opioids on NK activity have been assessed by in vitro studies. Several groups of investigators have shown that the endogenous opioid β-endorphin increases NK cell activity in vitro and that this effect can be reversed by naloxone, a specific opioid antagonist (Kay et al., Life Sci., 35:53–59, 1984; Mandler et al., J. Immunol, 136:934–939, 1986; Mathews et al., J. Immunol, 130:1658–1662, 1983). Met-enkephalin, another opioid peptide, also appears to enhance NK activity (Faith et al., Immunopathol, 31:412–418, 1984; Mathews et al., J. Immunol, 130:1658–1662, 1983; Wybran, Fed. Proc. 44:92–94, 1985), whereas conflicting results have been reported for Leu-enkephalin (Faith et al., Immunolpathol, 31:412–418, 1984; Mathews et al., J. Immunol, 130:1658–1662, 1983; Wybran, Fed. Proc., 44:92–94, 1985), α-endorphin (Kay et al., Life Sci., 35:53–59, 1984; Mandler et al., J. Immunol, 136:934–939, 1986) and γ-endorphin (Kay et al., Life Sci., 35:53–59, 1984; Mandler et al., J. Immunol, 136:934–939, 1986). Both Met and Leu-enkephalin are delta opioid receptor agonists. Laidow et al., J. Biol. Chem., 255:11908, (1980). Fewer studies of the effects of exogenous opioids on NK activity in vitro have been reported. Morphine enhanced NK activity in one study (Wybran, Fed. Proc., 44:92–94, 1985) but not in two others (Kay et al., Life Sci., 35:53–59, 1984; Mathews et al., J. Immunol, 130:1658–1662, 1983).

An inhibition of NK activity of cells from normal subjects and patients on methadone maintenance was observed in vitro only at methadone concentrations many orders of magnitude higher than those observed during any clinical use of methadone or compatible with life. Kreek, Ann. N.Y. Acad. Sci., 311:110–134, 1988; Ochshorn et al., Isr. J. Med. Sci., 26:421–425 1990.

The dynorphins are a group of peptides which bind with high affinity to opioid receptors in the brain and spinal cord. Although the dynorphins do not appear to be analgesic in the brain, they may be analgesic in the spinal cord. Dynorphin A (1-17) and its 13 amino acid fragment dynorphin A (1-13) were the first dynorphins isolated (Goldstein et al. Proc. Natl. Acad. Sci. USA, 76:6666–6670, 1979) and are the best characterized.

U.S. Pat. No. 4,462,941 refers to dynorphin analogs having at least 10 amino acids but less than 13. Such analogs are reported to potentiate the analgesic effect in tolerant hosts of narcotic analgesics.

U.S. Pat. No. 4,481,991 refers to dynorphin and dynorphin analogs and to their use in treating high blood pressure or disturbances of cardiac function.

U.S. Pat. Nos. 4,537,878, 4,757,049, and 4,801,614 refer to processes for modulating the immune system using various opioid agonists. In particular, U.S. Pat. No. 4,537,878 reports both increases and decreases in NK activity in individuals following administration of methionine enkephalin. Administration of enkephalins and related compositions is reported to have activity regulating viruses, bacteria, fungi, tumorous cells and parasites and generally all immune deficiencies associated with aging through the stimulation of T and NK cell populations. These patents, however, fail to teach or suggest the structural relationship by which methionine enkephalin or its stated equivalents increase or decrease NK activity.

PCT application PCT/US91/05518 published as WO 92/02547 refers to a method for stimulating or suppressing the immune system of a patient by administering different amounts of dynorphin in the acid or amide form. Stimulation of the immune system is reported with either the acid or amidated form of the dynorphins. However, only the acid form was reported to have a biphasic effect by both stimulating and suppressing the immune system. The amidated form of dynorphin was reported not to have the biphasic effect and only immune stimulation was observed.

Many immunological functions are directly effected by NK cells. In particular, NK cells are a primary defense against cells infected with virus. This activity of NK cells complicates and may reduce the efficacy of gene therapy involving the introduction of genetic material into an individual using a viral vector. Surprisingly little research has been reported evaluating the effects of NK activity in gene therapy.

Even though various systems involving different types of viral vectors may be efficient means of targeting cells with new genetic sequences, several factors decrease the efficacy of these vectors in providing gene therapy. Retroviral vectors for instance, randomly integrate into the cellular genome and therefore may interrupt current protein synthesis or be inserted in such a way as to prevent the integrated DNA sequence from functioning. Retroviruses may also integrate into other retroviruses thereby destroying the integrated DNA of both retroviruses. Such characteristics result in lower levels of desired end-product being synthesized. Additionally, many cell types do not react well to the prolonged in vitro culture often used during transduction. It is not unusual for as little as 25 percent of the original culture to survive and perform its intended function. The amount of vector-DNA actually expressed must therefore be safeguarded from any other type of attack which might reduce or eliminate efficiency once the vector is administered to those individuals in need of gene therapy.

NK cells present a significant problem for individuals undergoing gene therapy. The effect of any level of viral infection typically is in part to activate the immune system, particularly NK cells, in an effort to rid the body of the infecting virus. Since NK cells are not specific for particular antigenic determinants and do not require prior exposure for activation, it is possible for the immune system to mistake a "self" molecule infected with virus or one having undergone neoplastic-like changes as being foreign, in addition to destroying any cell transduced by a vector-DNA sequence. Such an immune response would be undesirable if the infecting virus is a recombinant virus containing desired therapeutic genetic material and the infected cells are those which correct for some defect by expressing the transfected genetic material. Thus, all cells infected by a vector-DNA sequence including but not limited to retroviruses, adeno-associated viruses, vaccinia and herpes simplex I would be potential targets for attack by NK cells.

SUMMARY OF THE INVENTION

This invention provides a method of suppressing the cytoxic activity of mammalian NK cells. The method comprises administering to an individual in need of treatment a dynorphin A peptide having the following structure:

(SEQ ID NO:8)

$X_{aa}-X_{aa}-X_{aa}-X_{aa}-X_{aa}-X_{aa}-X_{aa}-X_{aa}-X_{aa}-$
1                                    5
$X_{aa}-X_{aa}-X_{aa}-X_{aa}-X_{aa}-X_{aa}-X_{aa}-X_{aa}$
10                                15 wherein position one is selected from the group consisting of tyrosine, m-tyrosine and dopa. Positions 2,3,15,16 and 17 are neutral amino acids selected from the group consisting of glycine, serine, threonine, cysteine, tyrosine, asparagine, glutamine and alpha-amino isobutyric acid (AIB). The amino acid at position 4 is selected from the group consisting of phenylalanine, tyrosine, alpha-methylphenylalanine, and phenylalanine wherein the phenyl ring is substituted with a para-substituted electron withdrawing group such as a halogen or nitro group. Positions 5 and 14 are selected from the group of nonpolar hydrophobic amino acids consisting of isoleucine, valine, proline, phenylalanine, tryptophan and methionine.

Positions 6, 7 and 9 are most preferably arginine but may also be a positively charged amino acid selected from the group consisting of lysine, histidine, homoarginine or ornithine. Position 9, however, may also include proline.

The amino acids at position 8 and 12 are selected from the group of basic and neutral amino acids consisting of tyrosine, leucine, isoleucine and lysine. Position 10 is a basic amino acid or proline analog selected from the group consisting of proline, thioproline, 3,4-dehydroproline, 4-hydroxyproline and pipecolic acid. Finally, the amino acids at positions 11 and 13 are most preferably lysine, but may also be a positively charged amino acid selected from the group consisting of histidine, homoarginine or ornithine.

The amino acids of peptides suitable for use in the method of this invention may be of the d or l form.

The carboxyl terminal end of the dynorphin peptides suitable for decreasing NK activity has the formula:

$$\text{amino acids}_{(1 \text{ to } n-1)}\text{-}\underset{|}{\overset{H}{N}}\text{-}\underset{|}{\overset{H}{\underset{aa_n}{C}}}\text{-}\overset{O}{\overset{||}{C}}\text{-}N\diagdown^{R_1}_{R_2} \quad (2)$$

wherein aa is the side chain of the nth amino acid and n is the total number of amino acids in the dynorphin A polypeptide. $R_1$ and $R_2$ may be the same or different and may be hydrogen, alkyl or an optionally substituted benzylic group, or if one of $R_1$ and $R_2$ is a nitrogen containing moiety such as hydrazide the other is hydrogen. (SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8) When used to suppress NK activity in connection with providing gene therapy the dynorphin A peptide may also terminate in a carboxyl group. (SEQ ID NO:9, SEQ ID NO:10, SEQ ID NO:11, SEQ ID NO:12, SEQ ID NO:13, SEQ ID NO:14, SEQ ID NO:15, SEQ ID NO:16)

The peptide bond covalently linking the amino acids of dynorphin has the structure:

$$\text{amino acid(s)-}\overset{O}{\overset{||}{C}}\text{-}\underset{|}{\overset{R_3}{N}}\text{-amino acid(s)} \quad (3)$$

wherein $R_3$ is either hydrogen or $C_{1-4}$ alkyl and the alkyl group is either linear or branched. (SEQ ID NO:1, SEQ ID NO:2, SEQ ID NO:3, SEQ ID NO:4, SEQ ID NO:5, SEQ ID NO:6, SEQ ID NO:7, SEQ ID NO:8)

According to the method of this invention the dynorphin A peptide is administered in an amount sufficient to attenuate the cytotoxic activity of NK cells. Preferably, this is accomplished when such cells are contacted with dynorphin A polypeptide at a molar concentration of about $1 \times 10^{-7}$ to about $1 \times 10^{-2}$.

The method of the invention may be used to treat mammals, particularly humans who would benefit from a decrease in NK cell activity. The method of this invention is particularly useful for treating those individuals whose NK cells have been activated. This invention is also particularly useful to treat individuals who are recipients or expecting to be recipients of transplant tissue e.g., bone marrow tissue, liver, kidney, heart and lung. Other individuals in need of treatment may include those suffering from autoimmune disease.

Figure 2:
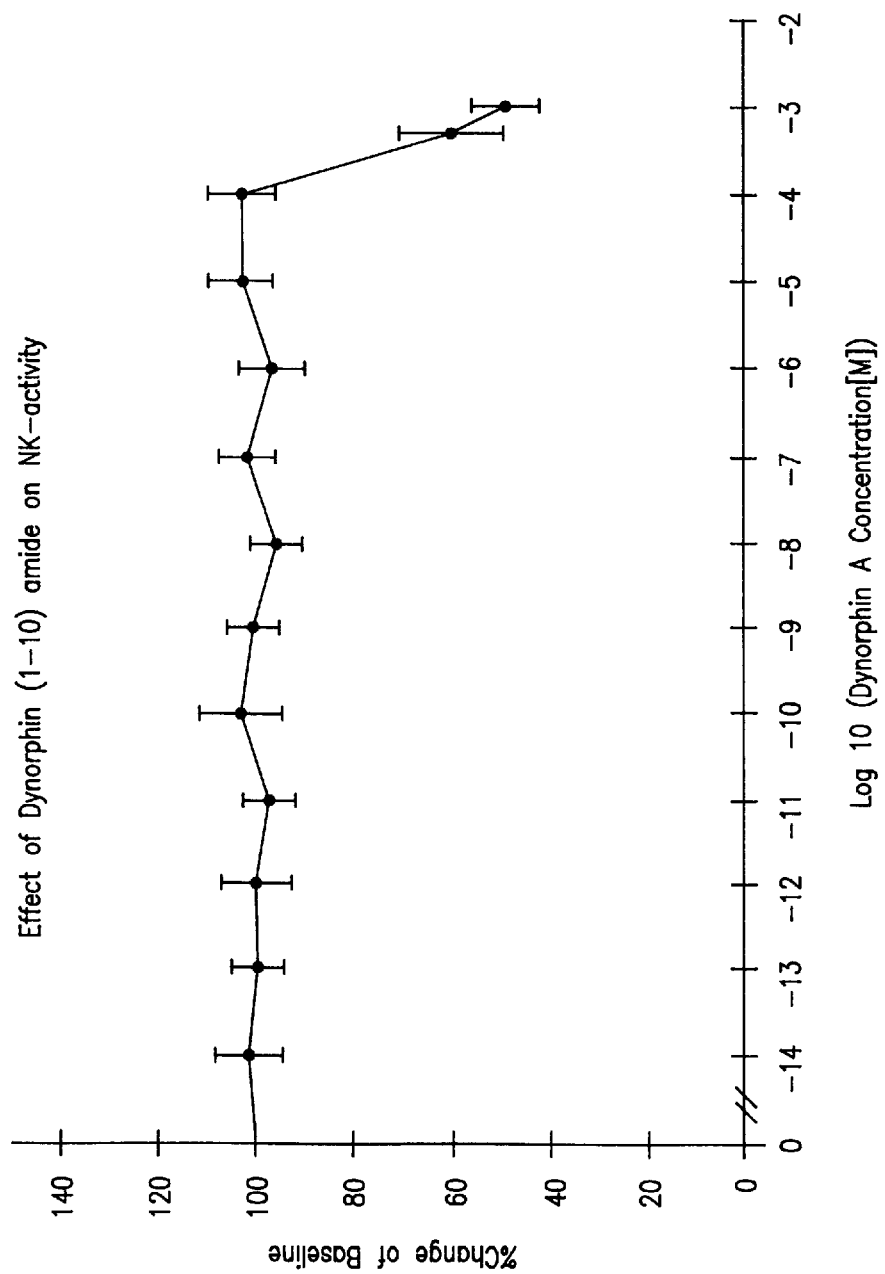
Figure 3A:
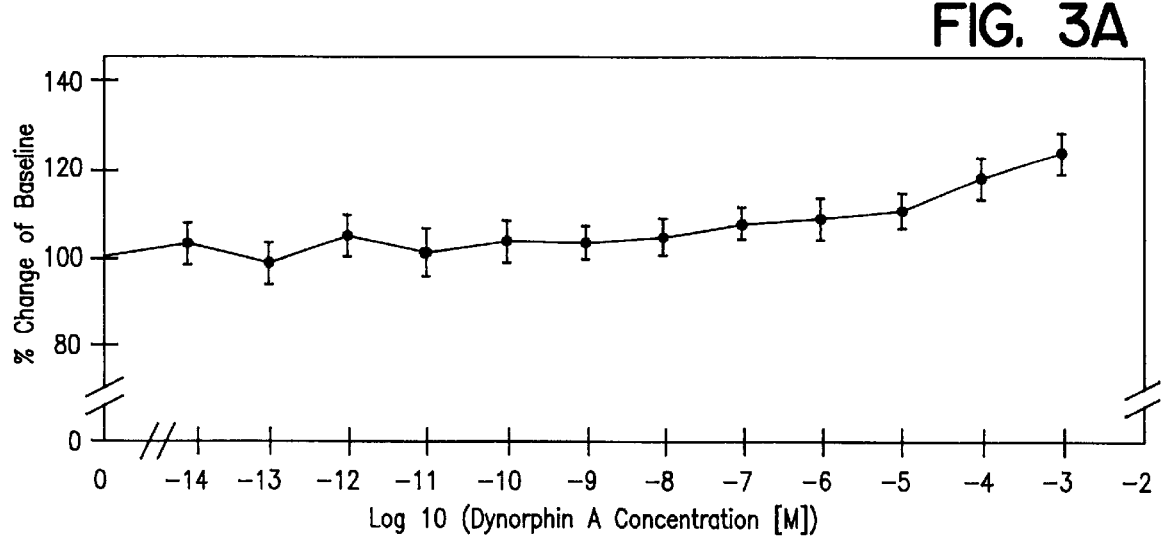
Figure 3B:
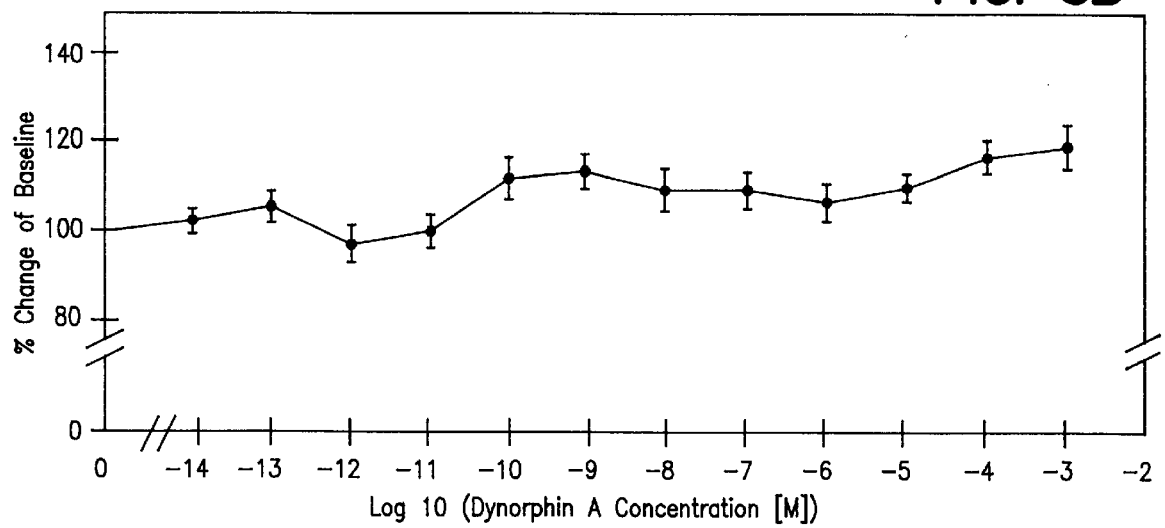
Figure 3C:
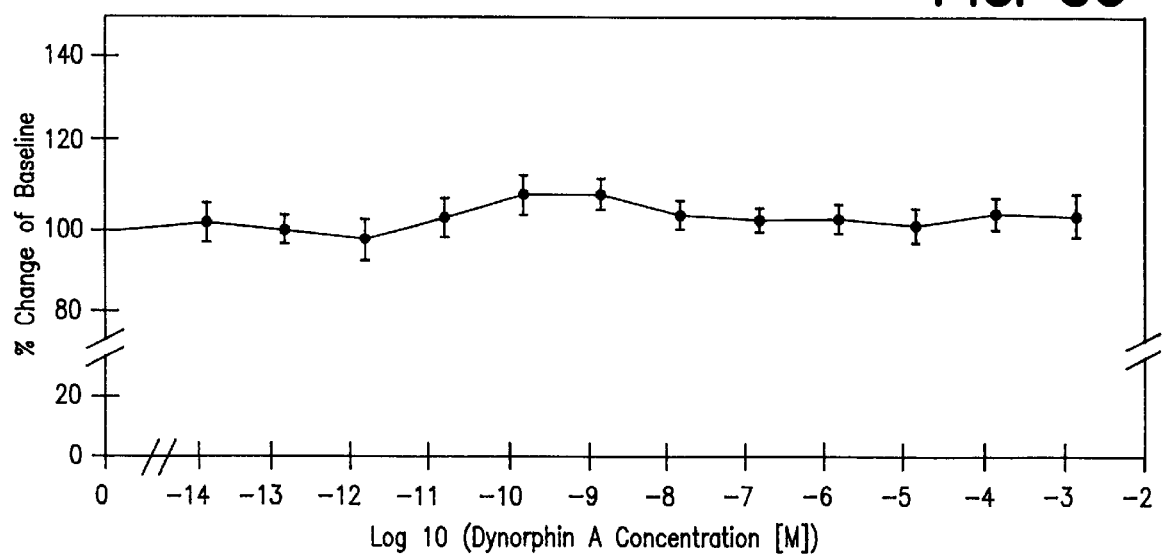

In addition, the method of this invention is useful for treating individuals in need of gene therapy involving infecting such an individual with a viral or viroid vector containing a therapeutic gene. When used to provide gene therapy, the carboxyl terminal of dynorphin A peptide administered to decrease NK cell activity may be as described in formula (2) or may be a carboxyl group.

An object of this invention is to provide a method for suppressing in vivo and when indicated, ex vivo the activity of NK cells.

Another object is to provide a method for decreasing the rejection of tissue in transplant recipients.

A further object is to provide a method for treating individuals suffering from various autoimmune diseases.

Another object is to provide a method for suppressing NK activity against cells infected with recombinant genes.

BRIEF DESCRIPTION OF THE DRAWINGS

FIG. 1 graphically illustrates the dose dependent suppression of NK-activity by dynorphin A (1-17). (SEQ ID NO:17)

FIG. 2 graphically illustrates the dose dependent suppression of NK-activity by dynorphin A (1-10) amide. (SEQ ID NO:1)

FIG. 3*a–c* graphically illustrates the absence of NK suppressing activity by dynorphin A (2-17), (SEQ ID NO: 18); dynorphin A (1-13), (SEQ ID NO:19); and dynorphin A (1-10), (SEQ ID NO:20).

DETAILED DESCRIPTION OF THE INVENTION

The invention provides a method of regulating the activity of a component of the immune system. Surprisingly, according to the method of the invention the cytotoxic activity of an individual's NK cells can be suppressed by administering to that individual a polypeptide having an amino acid sequence corresponding to dynorphin A or a dynorphin A analog.

Naturally occurring dynorphin A is a 17 amino acid peptide which has the formula:

Position 4 is preferably phenylalanine, but may be an alpha-alkylated phenylalanine, for example alpha-methyl phenylalanine, tyrosine or phenylalanine wherein the phenyl ring is substituted with a para-substituted electron withdrawing group such as a halogen or nitro group.

Positions 5 and 14 are most preferably leucine, but may be substituted with other nonpolar (hydrophobic) amino acids including but not limited to isoleucine, valine, proline, phenylalanine, tryptophan and methionine. More preferably the amino acid at position 5 is isoleucine, leucine or valine.

Positions 6,7,9,11 and 13 are most preferably arginine but may be another positively charged amino acid such as lysine, histidine, homoarginine or ornithine. The amino acid at position 9 may also be proline.

Positions 8 and 12 are most preferably isoleucine but may also be substituted with either a basic or neutral amino acid. Preferably the amino acid at position 8 is tyrosine, leucine isoleucine or lysine.

Position 10 is most preferably proline but may be another basic amino acid or proline analog such as thioproline, 3,4-dehydroproline, 4-hydroxyproline or pipecolic acid. Preferably the amino acid at position 10 is proline or lysine.

The amino acids which may be substituted for those of naturally occurring dynorphin A may be either of the d or l form.

The amino acids at positions 11 through 17 may be omitted or substituted depending on the structure of the carboxyl terminal which may terminate in either a carboxyl group or an optionally substituted amide group. (SEQ ID NO:9, SEQ ID NO:10, SEQ ID NO:11, SEQ ID NO:12, SEQ ID NO:13, SEQ ID NO:14, SEQ ID NO:15, SEQ ID NO:16) Dynorphin analogs which terminate in a carboxyl group must have a chain length of at least about fourteen amino acids. Preferably, substitutions of amino acids 11 through 17 are done in accordance with the principles outline above whereby neutral amino acids are substituted for neutral amino acids, basic amino acids are substituted for basic amino acids and acidic amino acids are substituted for acidic amino acids.

Tyr—Gly—Gly—Phe—Leu—Arg—Arg—Ile—Arg—Pro—Lys—Leu—Lys—Trp— (1)
1 5 10

Asp—Asn—Gln(SEQ ID NO:17).
15

The dynorphin A peptides and analogs which are suitable for use in the method of this invention have the amino acid tyrosine or a tyrosine analog at the amino terminal end of the peptide. This structure preserves the opiod-like activity of dynorphin A analogs. Additionally, this amino acid requirement at position one of the peptides suitable for use in this invention is based on our surprising finding that dynorphin A (2-17) (SEQ ID NO: 18) increases NK activity at concentrations above about 1 $\mu$M while dynorphin A (1-17) (SEQ ID NO:17) decreases NK activity at concentrations above about 0.1 $\mu$M. FIGS. 3 and 1, respectively.

Various amino acids may be substituted for the amino acids of formula 1. The tyrosine at position 1 may be substituted with m-tyrosine or dihydroxyphenylalanine (dopa). Preferably, position 1 is tyrosine.

The amino acids at positions 2, 3, 15, 16 and 17 are preferably glycine but may be substituted with other neutral amino acids including but not limited to serine, threonine, cysteine, tyrosine, asparagine, glutamine or alpha-amino isobutyric acid (AIB).

Preferably, the carboxyl terminal end of the dynorphin peptides and analogs which are suitable for use in this invention have the formula:

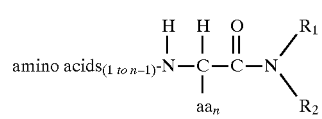

(2)

wherein aa is the side chain of the nth amino acid and n is the total number of amino acids in the dynorphin polypeptide; and $R_1$ and $R_2$ are the same or different and are selected from hydrogen, $C_{1-4}$ alkyl, an optionally substituted benzylic group, or when one of $R_1$ and $R_2$ is a nitrogen containing moiety such as hydrazide the other is hydrogen. More preferably, $R_1$ and $R_2$ are both hydrogen to form an amide. (SEQ ID NO:1, SEQ ID NO:2, SEQ ID NO:3, SEQ ID NO:4, SEQ ID NO:5, SEQ ID NO:6, SEQ ID NO:7, SEQ ID NO:8) It is believed, without being bound by theory, that substitution of the terminal carboxyl group serves to protect the amino terminal tyrosine residue from degradation.

Surprisingly, amidation of dynorphin A peptides converts peptides which do not exhibit NK suppressing activity to peptides which do suppress NK activity. For example, we have found that dynorphin A (1-10) (SEQ ID NO:20) did not exhibit any inhibition of NK activity, even at concentrations as high as 1 mM. FIG. 3. Dynorphin A (1-10) amide (SEQ ID NO:1) however, did cause a significant decrease in NK activity at concentrations above about 100 μM. FIG. 2. Accordingly, the use of other dynorphin A analogs which have been modified to protect the amino acid residue at position one would also be useful in the methods of this invention.

When used to provide gene therapy, the structure $$-\overset{O}{\underset{\|}{C}}-N\overset{R_1}{\underset{R_2}{\diagdown}}$$

of formula (2) may alternatively be $$-\overset{O}{\underset{\|}{C}}-OH$$

such that the $$-N\overset{R_1}{\underset{R_2}{\diagdown}}$$

structure is substituted with a hydroxyl group.

The peptide bond covalently linking together the amino acids of dynorphin A and dynorphin analogs useful in this invention has the structure:

$$\text{amino acid(s)}-\overset{O}{\underset{\|}{C}}-\overset{R_3}{\underset{|}{N}}-\text{amino acid(s)} \quad (3)$$

wherein $R_3$ is selected from hydrogen or $C_{1-4}$ alkyl and wherein the alkyl group is linear or branched. Preferably $R_3$ is hydrogen. (SEQ ID NO:10, SEQ ID NO:11, SEQ ID NO:12, SEQ ID NO:13, SEQ ID NO:14, SEQ ID NO:15, SEQ ID NO:16)

The ability of dynorphin analogs to suppress NK activity is also a function of the length of the peptide. For example, acid forms of dynorphin A (1-10) (SEQ ID NO:20) and dynorphin A (1-13) (SEQ ID NO:19) which are not amidated do not suppress NK activity whereas dynorphin A (1-17) (SEQ ID NO:17) does suppress NK activity. Because NK suppression is observed with dynorphin A (1-10) amide (SEQ ID NO:1), the amino acids at positions 11 through 17 of dynorphin A (1-17) (SEQ ID NO:17) are not required for NK suppression and may be substituted or deleted provided NK suppressing activity is retained. Accordingly, dynorphin A peptides and analogs in the acid form which are suitable for suppressing NK activity in accordance with this invention have a chain length of at least 14 amino acids. Preferably, the chain length is 17 amino acids. Without being bound by theory, the minimum chain length is that which is required to keep the carboxyl terminal end sufficiently separated from the amino terminal end so as to prevent loss of activity due to interaction with the tyrosine residue at position one.

When the dynorphin A peptide or analog is in the amide form the minimum chain length is that which retains NK suppressing activity, preferably between 10 and 17 amino acids in length. (SEQ ID NO:1, SEQ ID NO:2, SEQ ID NO:3, SEQ ID NO:4, SEQ ID NO:5, SEQ ID NO:6, SEQ ID NO:7, SEQ ID NO:8)

The various analogs of dynorphin A including naturally occurring dynorphin A which are suitable for use in the method of this invention activate opiate receptors. Activation of the kappa opiate receptor is particularly preferred. The ability of a dynorphin A peptide or analog to bind to the kappa opiate receptor may be determined by standard binding assays which are known to those of skill in the art. See Chaukin, C. et. al., *Science*, 215:413 (1982) and Jen, M. F. et al., *Eur. J. Pharmacology*, 91:95–99 1983.

Several dynorphin A analogs are known and have been described in the art. For example, U.S. Pat. No. 4,481,191, which is incorporated herein by reference, describes dynorphin A analogs which are stated to be useful for treating cardiovascular disorders. U.S. Pat. No. 4,462,941, which is also incorporated herein by reference, describes dynorphin A amide analogs which potentiate the analgesic effect of narcotics. PCT/US91/05518 application, which is also incorporated herein by reference, also describes dynorphin A analogs which are stated to be useful to stimulate or suppress the immune system. The various dynorphin A peptides and analogs described in the above patents and application are suitable for use in the method of this invention provided they satisfy the criteria described above. Dynorphin A and dynorphin A analogs may be synthesized by standard peptide synthetic techniques known to those skilled in the art and as described in U.S. Pat. No. 4,462,941 which is incorporated herein by reference.

The method of this invention is suitable for treating mammals preferably humans, for which suppression of NK cell activity would have beneficial effects. Examples of such persons are those who are transplant recipients of diverse types of tissue, in particular bone marrow; individuals whose immune activity is elevated as in individuals with autoimmune disease; and individuals undergoing or in need of gene therapy. Autoimmune disease would include autoimmune dysfunctions and autoimmune disorders. Examples of such autoimmune diseases include but are not limited to lupus erythematosis, rheumatoid arthritis, haemolytic anaemia, juvenile diabetes, Addison's diseases, thyrotoxicosis, autoimmune atropic gastritis, primary biliary cirrhosis and multiple sclerosis.

In another embodiment of this invention, dynorphin A and dynorphin A analogs are administered to those individuals in need of gene therapy. Gene therapy allows large quantities of various polypeptides to be produced either in vitro or in vivo by inserting the genetic sequence for a desired polypeptide into a replicating vector and then inserting that vector/DNA sequence into specific cells of an individual in need of treatment. Examples of diseases that may be suitable for gene therapy include, but are not limited to cystic fibrosis, β-thalassemia, sickle cell anemia, muscular dystrophy, rheumatoid arthritis, diabetes and various forms of cancer. Examples of cancer that may be suitable for gene therapy include, but are not limited to breast cancer, colon cancer, Gardner's multiple polyposis, acute myelogenous Leukemia, multiple myeloma and malignant melanoma.

To provide gene therapy to an individual, specific DNA sequences which code and express a desired protein are inserted into an appropriate vector complex which is then used to infect an individual in need of treatment. Various methods and vectors may be used for introducing a desired genetic sequence into an individual. The preferred and most often used method, incorporates the desired genetic sequence into the genome of a retrovirus to form chimeric genetic material. The genetically altered retrovirus may then be used to infect the appropriate target cells in vitro or in vivo. Preferably, the retrovirus is altered so the desired sequences are inserted into the genome of the target host cells and replicated without replicating the infecting virus. The result of a successful gene transfer via a retrovirus vector is a virally infected host cell which expresses only the desired gene product. For reviews on gene therapy using retroviral vectors see WO 92/07943 published May 14, 1992 "Retroviral Vectors Useful for Gene Therapy" and Richard C. Mulligan, "Gene Transfer and Gene Therapy: Principle, Prospects and Perspective" in *Etiology of Human Disease at the DNA Level*, Chapter 12. Jan Linsten and Alf Peterson, eds. Rover Press, 1991, which are incorporated herein by reference.

Other methods employed for gene therapy may include but are not limited to chemical modification to redirect a vector-DNA complex to a new target area. Additional viral vectors suitable for providing gene sequences include but are not limited to adeno-associated viruses, Herpes Simplex 1 Virus and vaccinia. Modified hepatitis B or C viruses and its delta agent RNA viroid-like structure may also be used as vectors targeted at the liver.

Human adeno-associated viruses (AAV), are a type of parvovirus that naturally integrates at a specific site in human chromosome 19. AAV may be modified so the AAV terminal repeats are combined with a desired genetic sequence to be cloned and then used as a vector for gene therapy in human lymphocytes. Replication of unmodified AAV requires co-infection with a helper virus, such as adenovirus or herpes simplex, however, the unmodified AAV will remain stably integrated without these assisting viruses. This stability makes AAV an excellent vector especially for combatting or correcting hemoglobinopathies such as, but not limited to, sickle cell disease and β-thalassemia. See: Carlos A. Muro-Cacho et al., "Gene Transfer in Human Lymphocytes Using a Vector Based on Adeno-Associated Virus" in *Journal of Immunotherapy* 11:231–237 (1992).

Recombinant vaccinia virus may also be used in gene therapy. Vaccinia is a pox-type virus containing large quantities of double-stranded DNA and replicates readily in host cell cytoplasm. Due to vaccinia's large DNA structure it has the capacity to encode over 200 separate polypeptides, including those necessary for replication of its genome. Foreign genes can be inserted into the vaccinia genome, with expression of the foreign gene occurring during the vaccinia replication cycle. With such large reproductive capacity, vaccinia has the ability to encode and express many gene sequences simultaneously. This would allow researchers to place the entire DNA sequence for extremely large polypeptides such as insulin or the various interleukins into individuals lacking the ability to produce an essential protein or into those individuals in need of chemotherapeutic treatment. Treatment and uses of vaccinia vectors are discussed in Macket, M. and Smith, G. L., *Journal of General Virology* 67:2067–82 (1986) and in WO 92/07944, "Vaccinia Vectors, Vaccinia Genes and Expression Products Thereof" published on May 14, 1992.

Herpes Simplex Virus 1 (HSV 1) may also be a useful vector in gene therapy. Howard J. Federoff et al., "Expression of Nerve Growth Factor In Vivo From a Defective Herpes Simplex Virus I Vector Prevents Effects of Axotomy on Sympathetic Ganglia", *Proceedings of the National Academy of Sciences* 89:1636–1640 (1992). HSV 1 is used in gene therapy primarily because of its advanced infection system. Following attachment of the HSV 1-DNA sequence to a target cell, the viral envelope fuses with the cell's plasma membrane permitting the viral nucleocapsid to enter directly into the cytoplasm and then into the host's nucleus. HSV 1 used in gene therapy is modified to remove all but the packaging sites and transcription units and then the desired DNA sequence is inserted. Gene therapy may also utilize chemical modification to alter or redirect infectivity of a selected vector-DNA (usually a retrovirus) toward cells possessing receptors unique for a selected chemical modifier. Additionally, viral specificity can be redirected by attaching antibodies toward various vector-DNA groups. Antibodies often used are anti-MHC I and anti-MHC II (MHC=Major Histocompatibility Complex). These antibody-virus-DNA complexes will then infect cells bearing the MHC antigen and replicate the inserted DNA sequence. See, Hirosha Neda et al., "Chemical Modification of an Ecotropic Murine Leukemia Virus Results in Redirection of Its Target Cell Specificity", *Journal of Biological Chemistry*, 22:14143–14146, 1991).

For treating individuals in need of gene therapy according to the method of this invention, the immune response which would normally be directed against such a viral infection is attenuated by treating the individual with dynorphin A or dynorphin A analogs in an amount sufficient to decrease the cytotoxic activity of NK cells. This administration of dynorphin A or dynorphin A analogs may occur before, during or after exposure to the chimeric virus.

The dynorphin A polypeptides and dynorphin A analogs are administered to an individual in need of treatment in amounts sufficient to suppress the cytotoxic activity of NK cells. Preferably, the polypeptides are administered to an individual in an amount sufficient to achieve a molar concentration in blood of about $1\times10^{-7}$ to $1\times10^{-2}$. Molar concentrations in blood of about $1\times10^{-6}$ to about $1\times10^{-3}$ are more preferred. According to the most preferred method of the invention, the polypeptides are administered in an amount sufficient to achieve a molar concentration in blood of about $1\times10^{-5}$ to about $1\times10^{-3}$. Because of the greater potential for cleavage or degradation of the acid form, the higher concentrations, i.e. $1\times10^{-5}$ to about $1\times10^{-2}$M, are preferred when the acid form is used to suppress NK activity.

Treatment may be monitored by assaying blood samples for NK activity. NK activity may be monitored by measuring the release of a marker from a NK target cell. As the NK activity is decreased through the administration of dynorphin A or dynorphin A analog a corresponding decrease in the release of the marker from the target cell should be observed. Preferably, the release of $^{51}Cr$ from K562 (ATCC #CCL 243) human erytholeukerice cells is assayed to assess NK activity.

If the transduced cells are dynorphin-sensitive and the therapeutic effect sought by administering the transduced cells would be inhibited or suppressed by the presence of dynorphin A, the administration of dynorphin A or dynorphin A analog would be discontinued or reduced prior to the introduction of the transduced cells into the patient. The molar concentration of dynorphin A would be reduced appropriately to allow the transduced cells to remain active and continue their intended therapeutic purpose. Transduced cells that may be sensitive to dynorphin A might include T-lymphocytes, B-lymphocytes and granulocytes.

The dynorphin A peptides and analogs which are administered according to this invention may be administered as a sterile pharmaceutical composition further comprising a biologically acceptable carrier including, but not limited to, saline, buffer, dextrose and water.

Means of administering the dynorphin A peptides and analogs may be oral, sublingual, intravenous, intraperitoneal, percutaneous or intranasal. Local administration directly to the site of action may also be desirable and may be accomplished through means known in the art including, but not limited to injection, infusion and implantation of a porous device in which the dynorphin A peptides or analogs are contained. Similarly to administration of other peptides, administration is preferably by a means which avoids contact with the gastrointestinal tract, unless that site is the desired site of action. If enteral administration is desired to avoid passage of dynorphin A to the liver and its subsequent degradation, administration is then preferably by sublingual or intranasal means or by other transmucosal routes.

EXAMPLES

Example I

Dynorphin A peptide and analog mediated Natural Killer Cell (NK) Suppression in vitro The NK suppression activity of dynorphin A (1-17) (SEQ ID NO:17), dynorphin A (1-10) (SEQ ID NO:20), dynorphin A (1-13) (SEQ ID NO:19), dynorphin A (2-17) (SEQ ID NO:18) and dynorphin A (1-10) amide (SEQ ID NO:1) was determined in vitro by measuring $^{51}$Cr release assay using human erythroleukemia cells (ATCC CCL 243) K562 as the targets. Peripheral blood mononuclear cells (PBMC) were separated from fresh heparinized blood using Ficoll-diatrizoate density gradient centrifugation. The cells were washed in RPMI 1640 medium supplemented with 10% fetal bovine serum, 1% L-glutamine and 1% penicillin-streptomycin. The K562 cells were labeled with 100 $\mu$Ci of $^{51}$Cr by incubation for 90 min. at 37° C. in a humidifier 5% $CO_2$ atmosphere. The PBMC cells were separately incubated with the various concentrations of the dynorphin peptides and analogs ($10^{-14}$ to $10^{-3}$M) for 15–30 min. After the 90 min incubation, the K562 cells were then washed four times and placed together with PBMC/dyn cells in duplicate tubes at a ratio of 1:50 (PBMC/dyn effector: K562 target) at a final volume of 1 ml and incubated in a humidified 5% $CO_2$ atmosphere for 4 hours. Maximal $^{51}$Cr release was determined by lysis of buffer washed and labelled K562 cells with 1% Triton X-100 solution. Spontaneous release was determined by incubation of labelled K562 cells with medium alone and baseline NK activity was determined by incubation of labelled K562 cells with the target cells alone. After incubation, 0.5 ml of supernatant was removed and radioactivity was counted. Cytotoxicity was calculated by using the mean of values as follows:

$$\% \text{ cytotoxicity} = \frac{\text{cpm sample} - \text{cpm spontaneous}}{\text{cpm maximal} - \text{cpm spontaneous}} \times 100$$

NK suppression was observed for the cells incubated with dynorphin A (1-10) amide (SEQ ID NO:1) and dynorphin A (1-17) (SEQ ID NO:17). FIGS. 1 and 2. Dynorphin A (1-10) (SEQ ID NO:20) did not cause any significant change in NK activity (FIG. 3) whereas dynorphin A (1-13) (SEQ ID NO:19) and dynorphin A (2-17) (SEQ ID NO:18) caused an increase in NK activity. FIG. 3.

Example II

NK Cell Suppression in Gene Therapy for Metastatic Melanoma

Suppression of natural killer cell activity during gene therapy for metastatic melanoma is performed after retroviral transduction of the interleukin-2 and the neomycin-resistance marker genes (NeoR) into human tumor-infiltrating lymphocytes (TIL). TIL cells are lymphoid cells that infiltrate solid tumors and possess unique lytic qualities, especially for autologous tumors. The combination of TIL cells and interleukin-2 can mediate substantial tumor regression in patients with advanced stages of melanoma because interleukin-2 acts as a stimulant for TIL production. If the gene for interleukin-2, therefore, is inserted into TIL cells in vitro the TIL cells when reintroduced into patients with autologous tumors such as metastatic melanoma will stimulate additional TIL production in vivo as a result of the continuous expression of interleukin-2. This enhancement of TIL cell activity and cell recruitment should further the activity against tumor cells resulting in reduction or eradication of the tumor. NK activity is reduced by administering dynorphin A or a dynorphin A analog (SEQ ID NO:9, SEQ ID NO:10, SEQ ID NO:11, SEQ ID NO:12, SEQ ID NO:13, SEQ ID NO:14, SEQ ID NO:15, SEQ ID NO:16) to increase the proportion of virally transformed TIL cells which survive NK attack. See Rosenberg, S. A. et.al., "Gene Transfer into Humans—Immunotherapy of Patients with Advanced Melanoma, Using Tumor-Infiltrating Lymphocytes Modified by Retroviral Gene Transduction", N. Engl. J. Med. 1990; 9:570–578.

Protocol

Tissue resected from tumor masses of patients with metastatic melanoma is grown in culture to isolate TIL cells using the techniques described in Rosenberg, S. A. et al., "Use of tumor-infiltrating lymphocytes and interleukin-2 in the immunotherapy of patients with metastatic melanoma: a preliminary report", N. Engl. J. Med. 1988; 319:1676–80 and Topalian, S. L., et al, "Expansion of human tumor infiltrating lymphocytes for use in immunotherapy trials", J. Immunol. Methods 1987; 102:127–41.

After the TIL cells are isolated and have been in culture for 8 to 19 days, the cells are transduced using the Moloney murine leukemia retrovirus LNL6. In this derivative of the Moloney murine leukemia virus, the gag, pol, and env genes are removed and the DNA sequence for interleukin-2 and the NeoR gene for neomycin phosphotransferase is inserted. This specific virus has a mutation in the gag gene which prevents the production of any viral proteins.

LNL6 virions produced by a retroviral "packaging" cell line infected with the LNL6 virus, PA317/LNL6, are grown in Dulbecco's modified Eagle's medium containing high levels of glucose and glutamine (12-604B, Whittaker Bioproducts) and 10 percent heat-inactivated fetal bovine serum (A-1111-L, Hyclone). Supernatants from the PA317/LNL6 cultures approaching confluence are harvested, pooled, filtered through 0.45-$\mu$m filters, titered on NIH/3T3 cells and then frozen at −70° C. until immediately before use. The retrovirus-containing supernatant is then tested for aerobic and anaerobic bacteria and mycoplasma. MAP tests, tests for lymphocytic choriomeningitis virus, and an S+L− assay for ecotropic, xenotropic, and amphotrophic helper viruses are also performed. General safety tests in mice and guinea pigs are additionally performed in accordance to FDA requirements.

One third to one half of the TIL cells are exposed to the LNL6 supernatant once the total cell count in the cultures of TIL cells have reached a cell count of about 1.2 to 7.6×$10^8$ cells. The ratio of virions to cells should range from 1.3 to 2.3 in the presence of 5 $\mu$g of protamine per milliliter of solution in an 800-ml tissue-culture flasks containing 200 ml of medium per flask. The cells are incubated in the presence of the virions for two hours at 37° C. The cells are washed and subcultured at a density of $10^6$ cells per milliliter. The transduction procedure is repeated until a recovery rate of 74 to 100 percent is obtained.

Before the infusion of TIL cells into the patient, the various cultures are screened according to their expression of cell-surface markers by flow cytometry. Their lytic properties against autologous tumors, allogeneic tumors, and chromium-51-release assays against NK-sensitive K562 and NK-insensitive Daudi cell lines is also determined. A standard limulus assay is conducted for endotoxins and Southern blot and neomycin phosphotransferase assays are performed to confirm the presence and expression of the NeoR gene and thus the successful transduction of the accompanying interleukin-2 sequence.

Approximately two weeks before the planned reintroduction of transduced TIL cells into the patient undergoing gene therapy, the patient would begin a course of treatment with dynorphin A peptide or analog. The patient would receive an amount of dynorphin A or dynorphin A analog sufficient to achieve a molar concentration in the blood of about $1 \times 10^{-4}$ to about $1 \times 10^{-3}$. The chosen dynorphin is administered every 1 to 3 hours until approximately 48 hours before the patient is infused with recombinant TIL cells at which point administration of dynorphin A peptide or analog is stopped. This is to minimize exposure of the TIL cells to dynorphin A or its analogs which may directly reduce the cytotoxic activity of TIL cells.

After 48 hours, or when the level of dynorphin A peptide in the patient has reached a molar concentration below about $1 \times 10^{-7}$, the transduced cells may then be introduced into the patient. A maximum of $2 \times 10^{11}$ cells per infusion of transduced TIL/interleukin-2 is administered in one to three infusions of 200 to 250 ml each over a 30 to 60 minute period.

After an interval of 10 to 22 days of recovery, the patient returns for a second cycle of TIL/interleukin-2, with the patient again receiving dynorphin A peptide or analog treatment up until 48 hours before resumption of the TIL/interleukin-2 infusions.

Two months after the start of treatment, radiographs, scans and assays are obtained to evaluate the status of the cancer. Patients with stable or regressing cancer are given a second course of treatment.

With the introduction of a dynorphin A peptide or analog for limited intervals during the course of treatment, patients may receive full benefit of the transduced TIL/interleukin-2 without NK cytotoxicity towards the reintroduced TIL cells.

While we have hereinbefore described a number of embodiments of this invention, it is apparent that the basic constructions can be altered to provide other embodiments which utilize the methods of this invention. Therefore, it will be appreciated that the scope of this invention is defined by the claims appended hereto rather than by the specific embodiments which have been presented hereinbefore by way of example.

We claim:

1. A method of suppressing the cytotoxic activity of NK cells in a mammal, said method comprising administering to said mammal in an amount sufficient to inhibit the cytotoxic activity of said NK cells, a dynorphin A peptide having an amino acid sequence of ten to seventeen amino acids, and wherein said amino acid sequence is the sequence as shown in formula I Formula 1 (SEQ ID NO:8)
$X_{aa}-X_{aa}-X_{aa}-X_{aa}-X_{aa}-X_{aa}-X_{aa}-X_{aa}-X_{aa}-$
1               5
$X_{aa}-X_{aa}-X_{aa}-X_{aa}-X_{aa}-X_{aa}-X_{aa}-X_{aa}$
       10      15 wherein the amino acid at position 1 is selected from the group consisting of tyrosine, m-tyrosine and dihydroxyphenylalanine (dopa);

positions 2, 3, 15, 16 and 17 are neutral amino acids selected from the group consisting of glycine, serine, threonine, cysteine, tyrosine, asparagine and glutamine and alpha-amino isobutyric acid (AIB);

position 4 is an amino acid selected from the group consisting of phenylalanine, tyrosine, alpha-methylphenylalanine, and phenylalanine wherein the phenyl ring is substituted with a para-substituted electron withdrawing group such as a halogen or nitro group;

positions 5 and 14 are nonpolar, amino acids selected from the group consisting of leucine, isoleucine, valine, proline, phenylalanine, tryotophan and methionine;

positions 6, 7, 11 and 13 are positively charged amino acids selected from the group consisting of arginine, lysine, histidine, homoarginine and ornithine;

positions 8 and 12 are amino acids selected from the group of basic and neutral amino acids consisting of tyrosine, leucine, isoleucine and lysine;

position 9 is a positively charged amino acid selected from the group consisting of proline, arginine, lysine, histidine, homoarginine and ornithine;

position 10 is a basic amino acid or proline analog selected from the group consisting of thioproline, 3,4-dehydroproline, 4-hydroxyproline, proline and pipecolic acid;

wherein the amino acids are selected from d and 1 forms; and wherein the carboxyl terminal end of the dynorphin A peptide is an amide.

2. The method according to claim 1 wherein the amidated dynorphin A peptide is dynorphin A (1-10) amide up to and including dynorphin A (1-17) amide.

3. The method according to claim 1 wherein the dynorphin A peptide is administered to an individual in amount sufficient to achieve a molar concentration in blood of about $1 \times 10^{-7}$ to about $1 \times 10^{-2}$.

4. The method according to claim 4 wherein the dynorphin A peptide is administered to an individual in amount sufficient to achieve a molar concentration in blood of about $1 \times 10^{-6}$ to about $1 \times 10^{-3}$.

5. The method according to claim 5 wherein the dynorphin A peptide is administered to an individual in amount sufficient to achieve a molar concentration in blood of about $1 \times 10^{-5}$ to about $1 \times 10^{-3}$.

6. The method according to claim 5, wherein the dynorphin A peptide is dynorphin A (1-10) amide.

7. The method according to claim 1 wherein the dynorphin A peptide is administered to an individual to decrease NK activity of individuals with an autoimmune disease.

8. The method according to claim 7 wherein the autoimmune disease is selected from the group consisting of lupus erythematosis, rheumatoid arthritis, haemolytic anaemia, juvenile diabetes, Addison's diseases, thyrotoxicosis, autoimmune atrophic gastritis, primary biliary cirrhosis and multiple sclerosis.

9. The method according to claim 7 wherein the dynorphin A peptide is administered in an amount sufficient to achieve a molar concentration in blood of about $1\times10^{-7}$ to about $1\times10^{-2}$.

10. The method according to claim 9 wherein the dynorphin A peptide is administered to an individual in an amount sufficient to achieve a molar concentration in blood of about $1\times10^{-6}$ to about $1\times10^{-3}$.

11. The method according to claim 10 wherein the dynorphin A peptide is administered to an individual in an amount sufficient to achieve a molar concentration in blood of about $1\times10^{-5}$ to about $1\times10^{-3}$.

12. The method according to claim 11 wherein therein the dynorphin peptide is dynorphin A (1-10) amide and dynorphin A (1-17) amide.

13. The method according to claim 1 wherein the dynorphin peptide is administered to suppress or decrease NK activity of individuals receiving transplant tissue.

14. The method of claim 13 wherein the transplant tissue is selected from the group consisting of liver, kidney, heart, lung and bone marrow.

15. The method according to claim 13 wherein the dynorphin A peptide is administered to an individual in an amount sufficient to achieve a molar concentration in blood of about $1\times10^{-7}$ to about $1\times10^{-2}$.

16. The method according to claim 15 wherein the dynorphin A peptide is administered to an individual in an amount sufficient to achieve a molar concentration in blood of about $1\times10^{-6}$ to about $1\times10^{-3}$.

17. The method according to claim 16 wherein the dynorphin A peptide is administered to an individual in amount sufficient to achieve a molar concentration in blood of about $1\times10^{-5}$ to about $1\times10^{-3}$.

18. The method according to claim 17 wherein the dynorphin A peptide is dynorphin A (1-10) amide.

* * * * *

UNITED STATES PATENT AND TRADEMARK OFFICE
CERTIFICATE OF CORRECTION

PATENT NO. : 5,817,628

DATED : October 6, 1998

INVENTOR(S) : Lampropoulos, et al

It is certified that error appears in the above-identified patent and that said Letters Patent is hereby corrected as shown below:

COLUMN 1, LINE 3, before "FIELD OF THE INVENTION", insert --This invention was made with Government support under NIH grant DA00049 awarded by the National Institutes of Health. The government has certain rights in this invention.--

Signed and Sealed this

Third Day of April, 2001

Attest:

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO. : 5,817,628
DATED : October 6, 1998
INVENTOR(S) : Mary Jeanne Kreek

Page 1 of 1

It is certified that error appears in the above-identified patent and that said Letters Patent is hereby corrected as shown below:

Column 1,
Line 3, before "FIELD OF THE INVENTION", insert -- This invention was made with Government support under NIH grant DA00049 awarded by the National Institutes of Health. The government has certain rights in this invention. --

This certificate supersedes certificate of correction issued April 3, 2001.

Signed and Sealed this

Eighth Day of January, 2002

Attest:

Attesting Officer

JAMES E. ROGAN
*Director of the United States Patent and Trademark Office*